US 6,469,151 B1
(12) United States Patent
Egholm et al.

(10) Patent No.: US 6,469,151 B1
(45) Date of Patent: Oct. 22, 2002

(54) PNA-DNA CHIMERIC PROBE ARRAYS AND METHODS OF USE

(75) Inventors: Michael Egholm, Woodbridge, CT (US); Caifu Chen, Palo Alto, CA (US)

(73) Assignee: PE Corporation, Foster City, CA (US)

( * ) Notice: Subject to any disclaimer, the term of this patent is extended or adjusted under 35 U.S.C. 154(b) by 0 days.

(21) Appl. No.: 09/881,557

(22) Filed: Jun. 14, 2001

Related U.S. Application Data

(63) Continuation of application No. 09/416,003, filed on Oct. 8, 1999, now Pat. No. 6,297,016.

(51) Int. Cl.$^7$ .................. C07H 21/00; C07H 21/02; C07H 21/04; C12Q 1/68
(52) U.S. Cl. ............... 536/23.1; 536/22.1; 536/24.3; 536/25.3; 435/6
(58) Field of Search ................ 536/22.1, 23.1, 536/26.3, 25.3; 435/6

(56) References Cited

U.S. PATENT DOCUMENTS 6,063,571 A 5/2000 Uhlmann et al. ............... 435/6

FOREIGN PATENT DOCUMENTS

| EP | 0829542 | 9/1997 |
| WO | WO 95/08556 | 3/1995 |
| WO | WO 96/31622 | 10/1996 |
| WO | WO 99/49293 | 9/1999 |

OTHER PUBLICATIONS

Weiler et al. Hybridization based DNA screening on peptide nucleic acid (PNA) oligomer arrays. Nucleic Acids Research, 1997, vol. 25, No. 14, pp. 2792–2799.*
Lutz et al., "Recognition of Uncharged Polyamide–Linked Nucleic Acid Analogs by DNA Polymerases and Reverse Transcriptases," American Chemical Society, 119:3177–3178 (1997).
Kozlov et al., "A Method for the 32 P Labelling of Peptides or Peptide Nucleic Acid Oligomers," Bioconjugate Chemistry, 9:415–417 (1998).
Matthews et al., "Review. Analytical Strategies for use of DNA probes," Analytical Biochemistry 169:1–25 (1988).
Stratagene Catalog, p. 39 (1988).
Grossman et al., "High–density multiplex detection of nucleic acid sequences: oligonucleotide ligation assay and sequence–coded separation," *Nucleic Acids Research* 22(*21*):4527–4534 (1994).
Uhlmann et al., "Synthesis and Properties of PNA/DNA Chimeras," *Angew. Chem. Ed. Engl.* 35(22):2632–2635 (1996).
Breipohl et al., "Novel Synthetic Routes to PNA Monomers and PNA–DNA Linker Molecules," *Tetrahedron Letters* 53:14671–14686 (1997).
van der Laan et al., "A Convenient Automated Solid–Phase Synthesis of PNA–(5')–DNA–(3')–PNA Chimera," *Tetrahedron Letters* 38 (*13*):2249–2252 (1997).
Vinayak et al., "Automated Chemical Synthesis of PNA and PNA–DNA Chimera on a Nucleic Acid Synthesizer," *Nucleosides & Nucleotides* 16(*7–9*):1653–1656 (1997).
Koppitz et al., "Formation of Oligonucleotide–PNA–Chimeras by Template–Directed Ligation," *J. Am. Chem. Soc.* 120:4563–4569 (1998).
Eugen Uhlmann, "Peptide Nucleic Acids (PNA) and PNA–DNA Chimeras: From High Binding Affinity towards Biological Function," *Biol. Chem.* 379:1045–1052 (1998).
Lutz et al., "Synthesis of a Monocharged Peptide Nucleic Acid (PNA) Analog and Its Recognition as Substrate by DNA Polymerases," *Nucleosides & Nucleotides* 18 (*3*):393–401 (1999).

* cited by examiner

Primary Examiner—Jezia Riley
(74) Attorney, Agent, or Firm—Alex Andrus

(57) ABSTRACT

The invention provides methods, kits, and compositions for ligation of PNA-DNA chimeric probes and oligonucleotides when they are hybridized adjacently to template nucleic acids using ligases and ligation reagents. Structural requirements of the chimeras for ligation include 5 to 15 contiguous PNA monomer units, 2 or more contiguous nucleotides, and a 3' hydroxyl or 5' hydroxyl terminus. The chimera and/or oligonucleotide may be labelled with fluorescent dyes or other labels. The methods include, for example, oligonucleotide-ligation assays (OLA) and single nucleotide polymorphism detection.

17 Claims, 19 Drawing Sheets

Figure 2A:
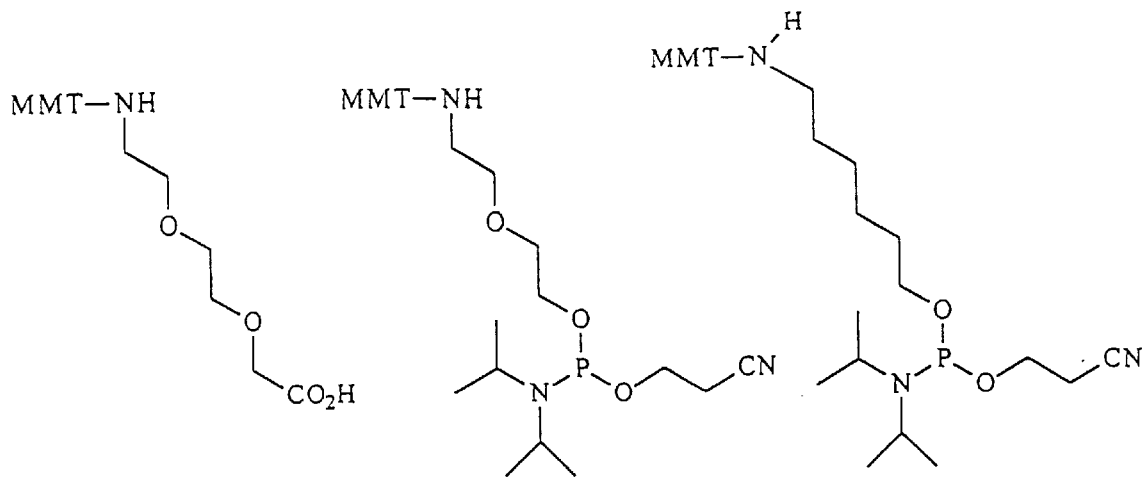

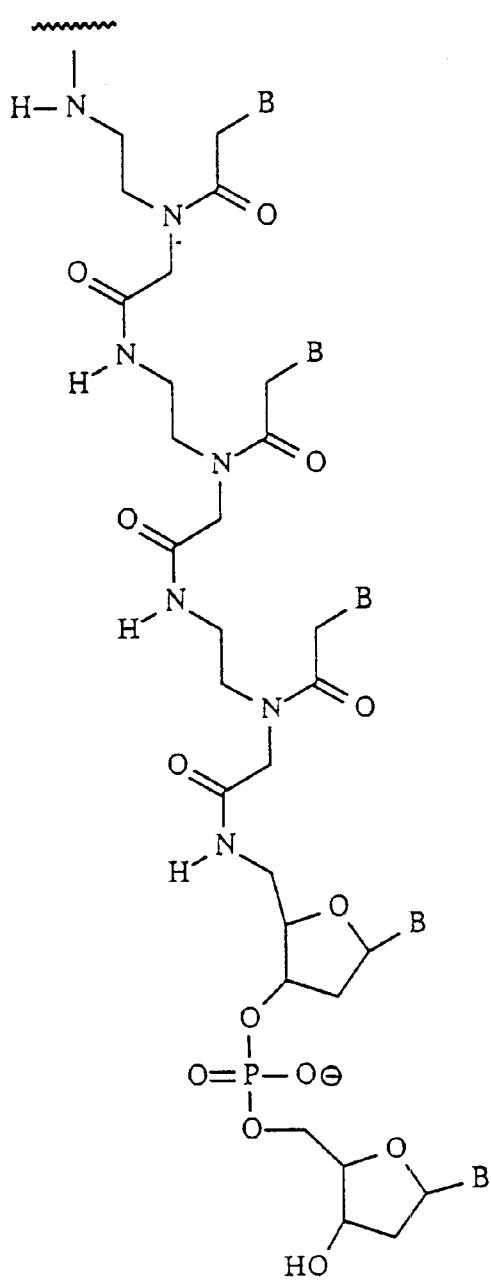
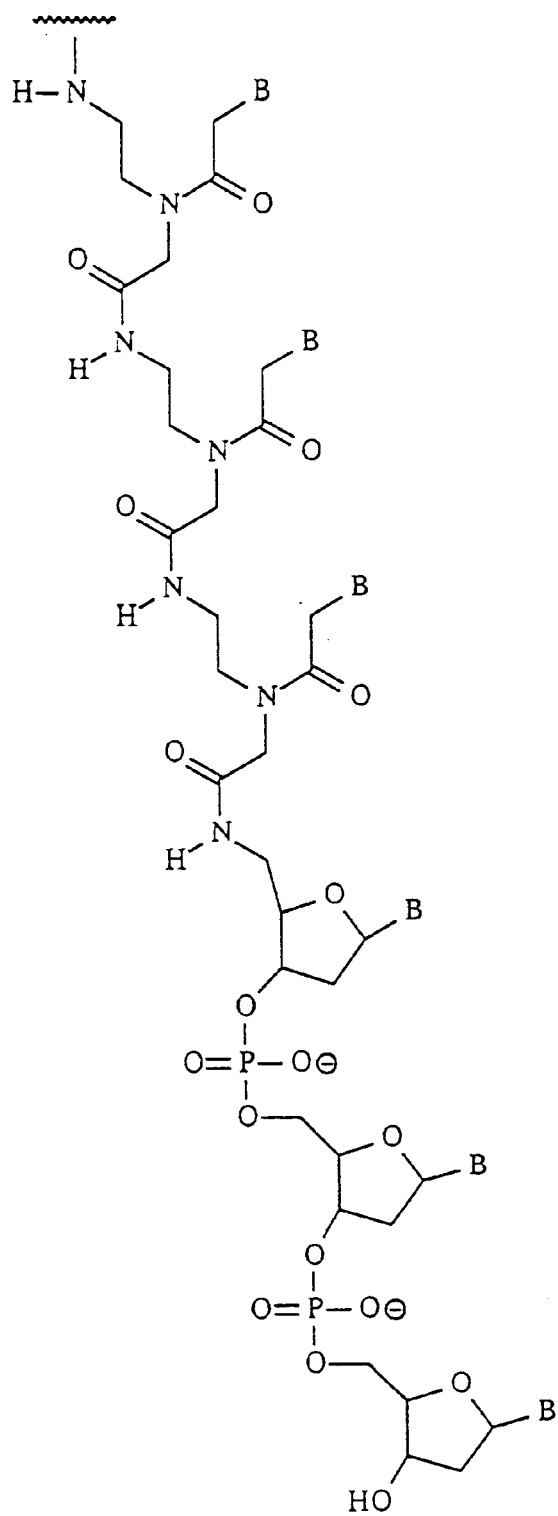
Figure 1A
Figure 1B

X = amide, urea, CH$_2$, O, or R

R = (CH$_2$)$_n$ or (CH$_2$CH$_2$O)$_n$
    n = 1 - 10

Y = trifluoroacetyl, Fmoc, trityl, MMT, DMT

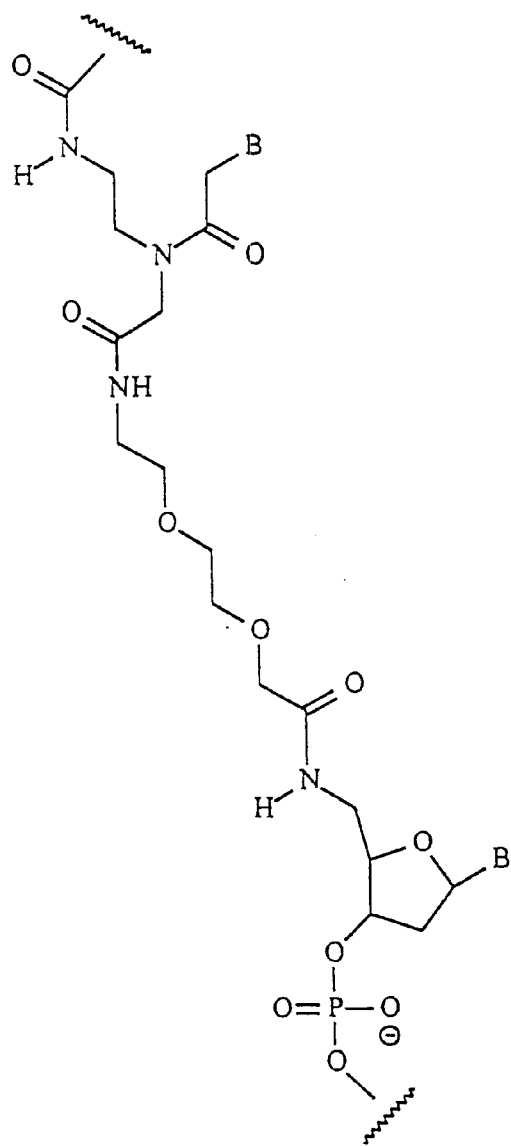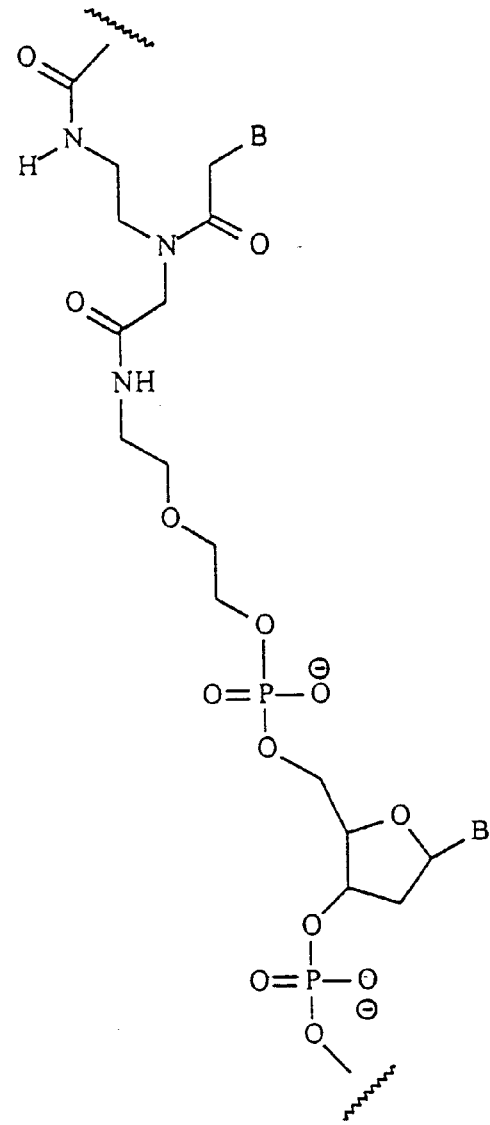
Figure 2B                    Figure 2C

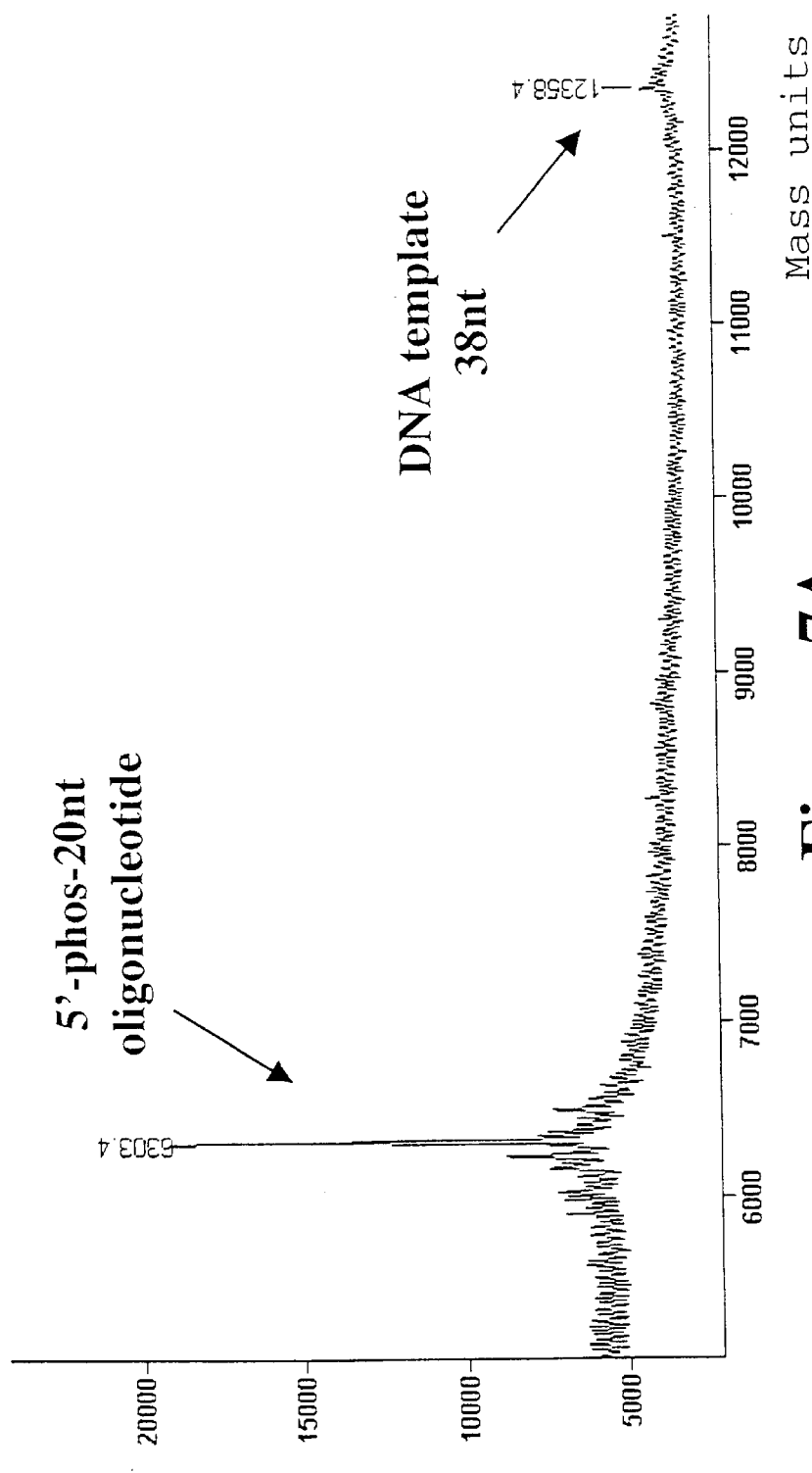

PNA OLA for human pCFTR621G-T: Exon 4

5'-phosphate, 3'-HEX oligonucleotide

Wild-type

PNA-DNA chimera          cct tct tat a-HEX 3'

5' C AAG GAA GTA tta
3' cg gac acg ttc ctt cat aat gga aga ata ttt agt ttg att 5'

Mutant (C to T)

act tct tat a-HEX 3'

5' C AAG GAA GTA tta
3' cg gac acg ttc ctt cat aat tga aga ata ttt agt ttg att 5'

Figure 9A

PNA OLA for human pCFTR1078delT: Exon 7

Wild-type

PNA-DNA chimera      5'-phosphate, 3'-TET oligonucleotide

5' CT TCT CAG GGt tc      5't ttg tgg tgt ttt t-TET 3'

3' ga aga aga aga gtc cca aga aac acc aca aaa ata gac acg 5'

Mutant (T deletion)

5' CT TCT CAG GGt tc      5' ttg tgg tgt ttt t-TET 3'

3' ga aga aga aga gtc cca ag- aac acc aca aaa ata gac acg 5'

Figure 9B

PNA OLA for human pCFTRG551D: Exon 11

5'-phosphate, 3'-FAM oligonucleotide

Wild-type

PNA-DNA chimera

```
5' TC TTG CTC GTt ga     c ctc cac tca gtg tga t-FAM 3'
3' c ttt aag aac gag caa ctg gag gtg agt cac act aag 5'
```

Mutant (C to T)

```
5' TC TTG CTC GTt ga     t ctc cac tca gtg tga t-FAM 3'
3' c ttt aag aac gag caa cta gag gtg agt cac act aag 5'
```

Figure 9C

PNA-DNA CHIMERIC PROBE ARRAYS AND METHODS OF USE

CROSS REFERENCE TO RELATED APPLICATION

This application is a continuation of application Ser. No. 09/416,003, filed Oct. 8, 1999, now U.S. Pat. No. 6,297,016 which is incorporated herein by reference.

I. FIELD OF THE INVENTION

The invention relates generally to the fields of enzymology and nucleic acid analogs. Specifically, this invention is directed to template-dependent ligation of PNA-DNA chimeras and oligonucleotides with ligase enzymes.

II. REFERENCES

Andrus, A. "Chemical methods for 5' non-isotopic labelling of PCR probes and primers" (1995) in *PCR 2: A Practical Approach*, Oxford University Press, Oxford, pp. 39–54.

Barany, F. "Genetic disease detection and DNA amplification using cloned thermostable ligase", Proc. Natl. Acad. Sci. USA 88:189–93 (1991).

Barany, F., Hood, L., Kaiser, R., Nickerson, D., Zebala, J. "New thermostable DNA ligase—obtd. using DNA from Thermus aquaticus strain HB8, used for ligation of oligonucleotides", WO 91/17239, Intl. Publ. Date Nov. 14, 1991.

Beaucage, S. and Iyer, R. "Advances in the synthesis of oligonucleotides by the phosphoramidite approach", Tetrahedron 48:2223–2311 (1992).

Benson, S., Menchen, S., Theisen, P., Uphadhya, K., and Hauser, J. "Aromatic-substituted xanthene dyes", WO 99/16832, Intl. Publ. Date Apr. 8, 1999.

Bergot, B., Chakerian, V., Connell, C., Eadie, J., Fung, S., Hershey, N., Lee, L., Menchen, S. and Woo, S. "Spectrally resolvable rhodamine dyes for nucleic acid sequence determination", U.S. Pat. No. 5,366,860, issued Nov. 22, 1994.

Blackburn, G. and Gait, M. Eds. "DNA and RNA structure" in *Nucleic Acids in Chemistry and Biology*, $2^{nd}$ Edition, (1996) Oxford University Press.

Breipohl, G., Will, D. W., Peyman, A. & Uhlmann, E. "Novel synthetic routes to PNA monomers and PNA-DNA linker molecules", Tetrahedron 53:14671–86 (1997).

Bronstein, I. and Voyta, J., "Methods of using chemiluminescent 1,2-dioxetanes" U.S. Pat. No. 4,931,223, issued Jun. 5, 1990.

Buchardt, O., Egholm, M., Nielsen, P., and Berg, R. "Peptide Nucleic Acids", WO 92/20702, Intl. Pub. Date Nov. 26, 1992.

Caruthers, M. and Beaucage, S. "Phosphoramidite compounds and processes", U.S. Pat. No. 4,415,732, issued Nov. 15, 1983.

Caruthers, M. and Matteucci, M. "Process for preparing polynucleotides", U.S. Pat. No. 4,458,066, issued July 3, 1984.

Clegg, R., "Fluorescence resonance energy transfer and nucleic acids", Meth. Enzymol., 211:353–388 (1992).

Cook, P. "PNA-DNA-PNA Chimeric macromolecules", U.S. Pat. No. 5,700,922, issued Dec. 23, 1997.

Delahunty, C., Ankener, W., Deng, Q., Eng, J. and Nickerson, D. "Testing the feasibility of DNA typing for human identification by PCR and an oligonucleotide ligation assay", Am. J. Hum. Genetics 58:1239–46 (1996).

Eghotm, M., Christensen, L., Dueholm, K., Buchardt, O., Coull, J., and Nielsen, P. "Efficient pH-independent sequence-specific DNA binding by pseudoisocytosine-containing bis-PNA", Nucleic Acids Res. 23:217–22 (1995).

Eghotm, M., Buchardt, O., Christensen, L., Behrens, C., Freier, S., Driver, D., Berg, R. and Kim, S. "PNA hybridizes to complementary oligonucleotides obeying the Watson-Crick hydrogen bonding rules", Nature 365:566–68 (1993).

Finn, P. J., Gibson, N. J., Fallon, R., Hamilton, A. & Brown, T. "Synthesis and properties of DNA-PNA Chimeric oligomers", Nucleic Acids Research 24:3357–63 (1996).

Flanagan, W., Wagner, R., Grant, D., Lin, K. and Matteucci, M. "Cellular penetration and antisense activity by a phenoxazine-substituted heptanucleotide", Nature Biotech. 17:48–52 (1999).

Fodor, S., Pirrung, M., Read, J., and Stryer, L. "Array of oligonucleotides on a solid substrate", U.S. Pat. No. 5,445,934, issued Aug. 29, 1995.

Grossman, P., Bloch, W., Brinson,E., Chang, C., Eggerding, F., Fung, S., Iovannisci, D., Woo, S. and Winn-Deen, E. "High-density multiplex detection of nucleic acid sequences: oligonucleotide ligation assay and sequence-coded separation", Nucl. Acids Res. 22:4527–34 (1994).

Guo, Z., Guilfoyle, R., Thiel, A., Wang, R. and Smith, L. "Direct fluorescence analysis of genetic polymorphisms by hybridization with oligonucleotide arrays on glass supports", Nucl. Acids Res. 22:5456065 (1994).

Jensen, K., Ørum, H., Nielsen, P., Norden, B. "Kinetics for hybridization of peptide nucleic acids (PNA) with DNA and RNA studied with the BIAcore technique", Biochem 36:5072–77 (1997).

Khan, S., Menchen, S., Rosenblum, B. "Substituted propargylethoxyamido nucleosides, oligonucleotides and methods for using same", U.S. Pat. No. 5,770,716, issued Jun. 23, 1998, and "Propargylethoxyamino nucleotides", U.S. Pat. No. 5,821,356, issued Oct. 13, 1998

Koppitz, M., Nielsen, P., Orgel, L. "Formation of Oligonucleotide-PNA-Chimeras by Template-Directed Ligation", J. Am. Chem. Soc., 120:4563–69 (1998).

Kornberg, A. in DNA Replication (1980), W. H. Freeman and Co., San Francisco, pp. 261–76.

Kricka, L. in *Nonisotopic DNA Probe Techniques* (1992), Academic Press, San Diego, pp. 3–28.

Kubista, M. and Svanvik, N. "Probe for analysis of nucleic acids", WO 97/45539, Intl. Publ. Date Dec. 4, 1997.

Kutyavin, I., Lukhtanov, E., Gamper, H. and Meyer, R. "Covalently linked oligonucleotide minor groove binder conjugates", WO 96/32496, Intl. Publ. Date Oct. 17, 1996.

Kyger, E., Krevolin, M. and Powell, M. "Detection of the hereditary hemochromatosis gene mutation by real-time fluorescence polymerase gene reaction and peptide nucleic acid clamping", Anal. Biochem. 260:142–48 (1998).

Landegren, U., Kaiser, R., Sanders, J. and Hood, L. "A ligase mediated gene detection technique", Science 241:1077–80 (1988).

Lee, L., Spurgeon, S., Rosenblum, B. "Energy transfer dyes with enhanced fluorescence", U.S. Pat. No. 5,800,996, issued Sep. 1, 1998.

Lutz, M., Will, D., Breipohl, G, Benner, S. and Uhlmann, E. "Synthesis of a monocharged peptide nucleic acid (PNA) analog and its recognition as substrate by DNA polymerase", Nucleosides & Nucleotides 18:393–401 (1999).

Lutz, M., Benner, S., Hein, S., Breipohl, G. and Uhlmann, E. "Recognition of uncharged polyamide-linked nucleic acid analogs by DNA polymerases and reverse transcriptatses", J. Am. Chem. Soc. 119:3177–78 (1997).

Menchen, S., Lee, L., Connell, C., Hershey, N., Chakerian, V., Woo, S. and Fung, S. "4,7-Dichlorofluorescein dyes as molecular probes", U.S. Pat. No. 5,188,934, issued Feb. 23, 1993.

Meyer, R. "Incorporation of modified bases in oligonucleotides" in *Protocols for Oligonucleotide Conjugates*, Ed. S. Agrawal (1994) Humana Press, Totowa, N.J., pp. 73–92.

Mullah, B. and Andrus, A. "Solid support reagents for the direct synthesis of 3'-labeled polynucleotides", U.S. Pat. No. 5,736,626, issued Apr. 7, 1998.

Nickerson, D., Kaiser, R., Lappin, S., Stewart, J., Hood, L. and Landegren, U. "Automated DNA diagnostics using an ELISA-based oligonucleotide assay" Proc. Natl. Acad. Sci USA 87:8923–27 (1990)

Nielsen, P., Egholm, M., Berg, R. and Buchardt, O. "Sequence-selective recogrution of DNA by strand displacement with a thymidine-substituted polyamide", Science 254: 1497–1500 (1991).

Rajur, S., Robles, J., Wiederholt, K., Kuimelis, R. and McLaughlin, L. "Hoechst 33258 tethered by a hexa (ethylene glycol) linker to the 5'-termini of oligodeoxynucleotide 15-mers: duplex stabilization and fluorescence properties", J. Organic Chem. 62:523–29 (1997).

Stanton, T., Schindele, D., Renzoni, G., Pepich, B., Anderson, N., Clagett, J. and Opheim, K. "Preparation and use of monomeric phthalocyanine reagents", WO 8804777, Intl. Publ. Date: Jun. 30, 1988.

Stetsenko, D. A., Lubyako, E. N., Potapov, V. K., Azhikina, T. L. & Sverdlov, E. "New Approach to Solid Phase Synthesis of Polyamide Nucleic Acids Analogues (PNA) and PNA-DNA Conjugates", Tetrahedron Lett. 37:3571–74 (1996).

Takahashi, M. etal, "Thermophilic DNA ligase", J. Biol. Chem. 259:10041–47 (1984).

Theisen, P., McCollum, C. and Andrus, A. "Fluorescent dye phosphoramidite labelling of oligonucleotides", in *Nucleic Acid Symposium Series* No. 27, Oxford University Press, Oxford, pp. 99–100 (1992).

Uhlmann, E. "Peptide nucleic acids (PNA) and PNA-DNA chimeras: from high binding affinity towards biological function", Biol. Chem. 379:1045–52 (1998).

Uhlmann, E., Will, D. W., Breipohl, G., Langner, D. & Ryte, A. "Synthesis and properties of PNA/DNA chimeras", Angew. Chem., Intl. Ed. Eng. 35:2632–35 (1996).

Uhlmann, E., Peyman, A., Breipohl, G. and Will, D. "PNA: Synthetic polyamide nucleic acids with unusual binding properties", Angew. Chem., Intl. Ed. Eng. 37:2796–2823 (1998).

Van der Laan, A.C. et al. "Optimization of the binding properties of PNA-(5')-DNA Chimerae", Bioorg. Med. Chem. Lent. 8:663–68 (1998).

Van der Laan, A., Brill, R., Kuimelis, R., Kuyl-Yeheskiely, E., van Boom, J., Andrus, A. and Vinayak, R. "A convenient automated solid-phase synthesis of PNA-(5')-DNA-(3')-PNA chimera", Tetrahedron Lett. 38:2249–52 (1997).

Vinayak, R., van der Laan, A., Brill, R., Otteson, K., Andrus, A., Kuyl-Yeheskiely, E. and van Boom, J. "Automated chemical synthesis of PNA-DNA chimera on a nucleic synthesizer", Nucleosides & Nucleotides 16:1653–56 (1997).

Vinayak, R. "Process and compounds for RNA synthesis", U.S. Pat. No. 5,281,701, issued Jan. 25, 1994.

Wengel, J. "Oligonucleotide analogs", WO 99/14226, Intl. Publ. Date Mar. 25, 1999.

Whiteley, N., Hunkapiller, M. and Glazer, A. "Detection of specific sequences in nucleic acids", U.S. Pat. No. 4,883, 750, issued 1989.

Will, D. W., Breipohl, G., Langner, D., Knolle, J. & Uhlmann, E. "The Synthesis of Polyamide Nucleic Acids using a Novel Monomethoxytrityl Protecting-Group Strategy", Tetrahedron 51:12069–12082 (1995).

III. BACKGROUND

The covalent joining of nucleic acid probes by ligase enzymes is one of the most useful tools available to molecular biologists. When two probes are annealed to a template nucleic acid where the two probes are adjacent and without intervening gaps, a phosphodiester bond can be formed by a ligase enzyme (Whiteley, 1989). The ligation bond is formed between a 5' terminus of one probe and the 3' terminus of the other probe.

The events of annealing and ligation each require a high level of fidelity, i.e. complementarity, between the sequences of the ligating probes and the template nucleic acid. Both events are inefficient when base-pairing mismatches occur. Generally, DNA ligase can join two adjacent probes only when they perfectly complement a denatured template nucleic acid, such as a PCR product (Landegren, 1988; Nickerson, 1990). Even a single nucleotide mismatch at, or near, the ligation site of the probes will prevent ligation of the annealed probes.

Oligonucleotide ligation assays detect the presence of specific sequences in target DNA sample. For example, allelic discrimination assays rely on probes representing the complementary sequences of the allelic forms to the target. Ligation to a common, second target-complementary probe indicates the presence of the polymorphic site (Whiteley, 1989; Landegren, 1988). Absence of ligation indicates the lack of the polymorphic site. Ligation can be detected through detectable labels on the allelic probe and electrophoretic separation of the ligation products (Grossman, 1994).

It is desirable to provide optimized probes and methods of annealing and ligation. Such methods would improve assays and tests that benefit from greater precision and accuracy.

IV. SUMMARY

The invention relates to chimeric molecules of PNA and DNA monomer units and their use in ligation methods to generate ligation products. The invention is based in part on the discovery that a ligase enzyme can ligate a PNA-DNA chimeric probe and a second probe under a broad range of experimental conditions and variables. PNA-DNA chimeras of the invention comprise at least two moieties covalently linked together, preferably: i) a contiguous moiety of 3 to 15 PNA monomer units, and ii) a contiguous moiety of at least two nucleotides. The nucleotide moiety has a ligatable terminus, such that the PNA-DNA chimera can be ligated to a second probe.

In a first aspect, the invention provides a method of producing a template-dependent ligation product by ligating a PNA-DNA chimeric probe, annealed to a template nucleic acid in the presence of a ligase and a ligation reagent, to a second probe annealed adjacent to the chimeric probe on the template nucleic acid. The second probe is capable of supporting template-dependent ligation. The second probe is a PNA-DNA chimera or an oligonucleotide. The second probe may be 5 to 100 monomer units or nucleotides (nt) in length. Preferably the second probe is 10 to 30 nt. Together, the chimeric probe and the second probe may be 10 to 100 nt.

In one illustrative embodiment of the invention, the PNA-DNA chimera has the formula:

$$P_x\text{-}L\text{-}N_y$$

where each P is independently a PNA monomer, x is an integer from 3 to 15, L represents a covalent linkage between P and N, each N is independently a nucleotide, y is an integer from 2 to 15, and the terminal N has either a 3' hydroxyl group or 5' hydroxyl group.

In a preferred embodiment, the PNA moiety, i.e., $P_x$, of the PNA-DNA chimera is a 2-aminoethylglycine peptide nucleic acid.

The DNA moiety, i.e., $N_y$, of the PNA-DNA chimera may be comprised of 2'-deoxynucleotides (DNA), ribonucleotides (RNA), and modified sugars or internucleotide linkages thereof, especially those that confer greater specificity, affinity, rate of hybridization, and chemical stability.

The chimera and/or the second probe may be labelled with a non-radioisotopic label such that the ligation product is non-radioisotopically labelled. In embodiments employing a labelled PNA-DNA chimera, the PNA-DNA chimera may be labelled at: (i) a nucleobase, e.g. the 7-deaza or C-8 positions of a purine or a deazapurine nucleobase, or the C-5 position of a pyrimidine nucleobase; (ii) a sugar; (iii) the PNA backbone; or (iv) an amino, a sulfide, a hydroxyl, and/or a carboxyl group. Preferably, the chimera is labelled at the amino terminus of the PNA moiety. In embodiments employing a labelled oligonucleotide, the oligonucleotide is preferably labelled at the opposite terminus from the ligation site, 3' or 5'. Alternatively, the oligonucleotide may be labelled at a nucleobase, but may also be labelled at other positions provided that the label does not interfere adversely with hybridization affinity or specificity, or with ligase efficiency. Labels may be fluorescent dyes, fluorescence quenchers, hybridization-stabilizers, energy-transfer dye pairs, electrophoretic mobility modifiers, chemiluminescent dyes, amino acids, proteins, peptides, enzymes, and affinity ligands. Preferably, the label is detectable upon illumination with light, e.g. laser sources at infrared, visible or ultraviolet excitation wavelengths.

The PNA and DNA moieties of the chimeric probe are covalently linked together. The linkage, L, between the PNA and DNA moieties may be a bond, e.g. the carbonyl-nitrogen bond in an amide group where the moieties are linked without intervening atoms, or a multi-atom linker. The linkage may comprise a phosphodiester group or a phosphoramidate group.

The template or target nucleic acid can be any nucleic acid or nucleic acid analog capable of mediating template-directed nucleic acid synthesis. Examples of suitable template nucleic acids include, e.g., genomic DNA, DNA digests, DNA fragments, DNA transcripts, plasmids, vectors, viral DNA, PCR products, RNA, and synthetic nucleic acids. The template nucleic acid may also be a metaphase or interphase chromosome. Preferably, the chromosome is denatured prior to PNA-DNA chimera hybridization and ligation. Template nucleic acids may be single-stranded or double-stranded and can range from as few as about 20–30 to as many as millions of nucleotides (nt) or base-pairs (bp), depending on the particular application.

The template nucleic acid, the PNA-DNA chimera, or the second probe may be immobilized on a solid substrate. Ligations may be conducted where one of the probes or template is attached to a solid support or surface.

V. BRIEF DESCRIPTION OF THE DRAWINGS

FIGS. 1A–1B Structures of PNA and PNA-DNA chimeras with: (1A) two 2'-deoxynucleotides, and (1B) three 2'-deoxynucleotides. B is a nucleobase.

FIGS. 2A–2C Structures of linker reagents and linkages: (2A) linker reagents to form amide and phosphodiester linkages, (2B) bis-amide linkage of 2-(2-aminoethoxy) ethoxyacetic acid, and (2C) amide, phosphate linkage of 2-(2-aminoethoxy)ethanol.

Figure 3A:
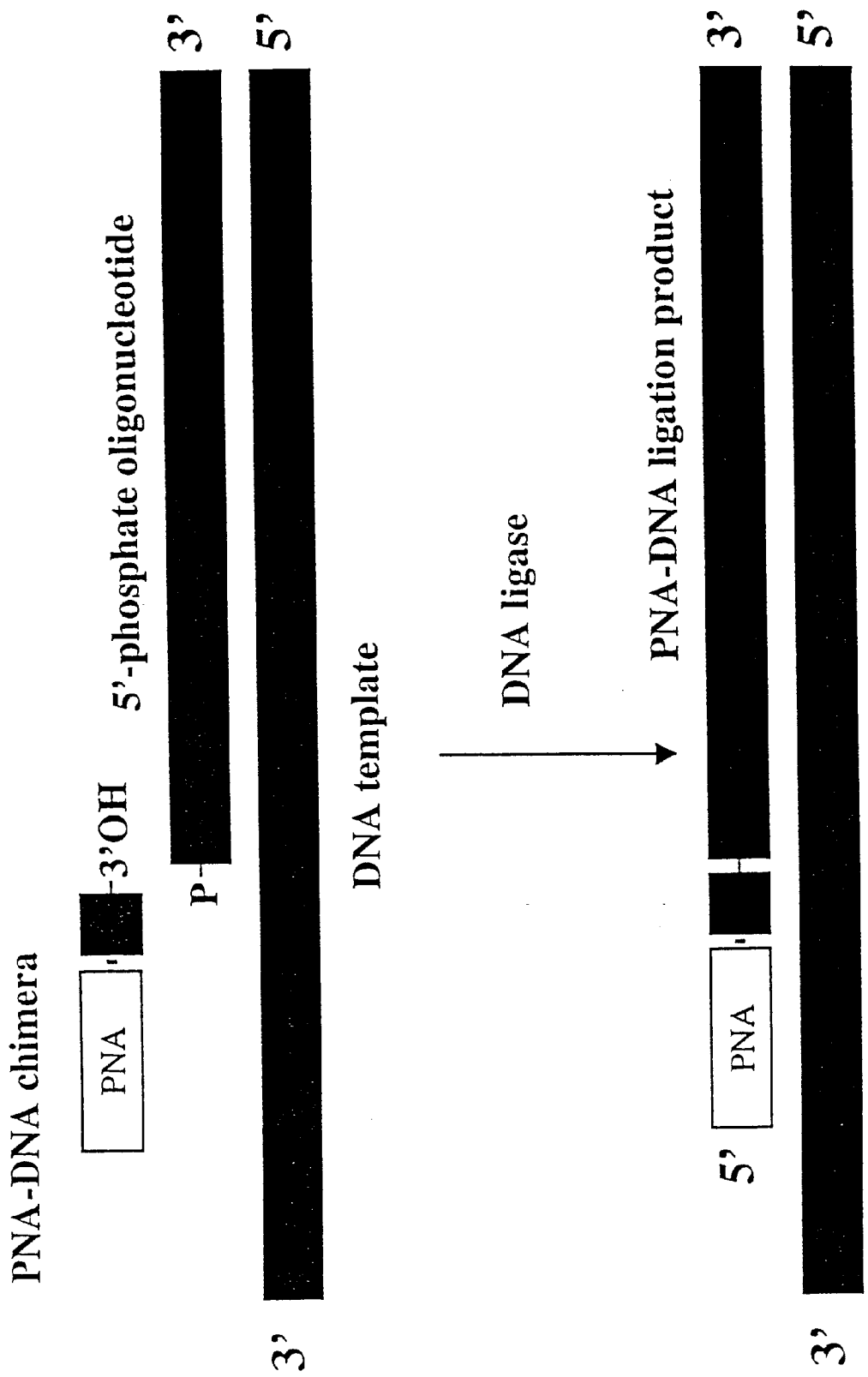
Figure 3B:
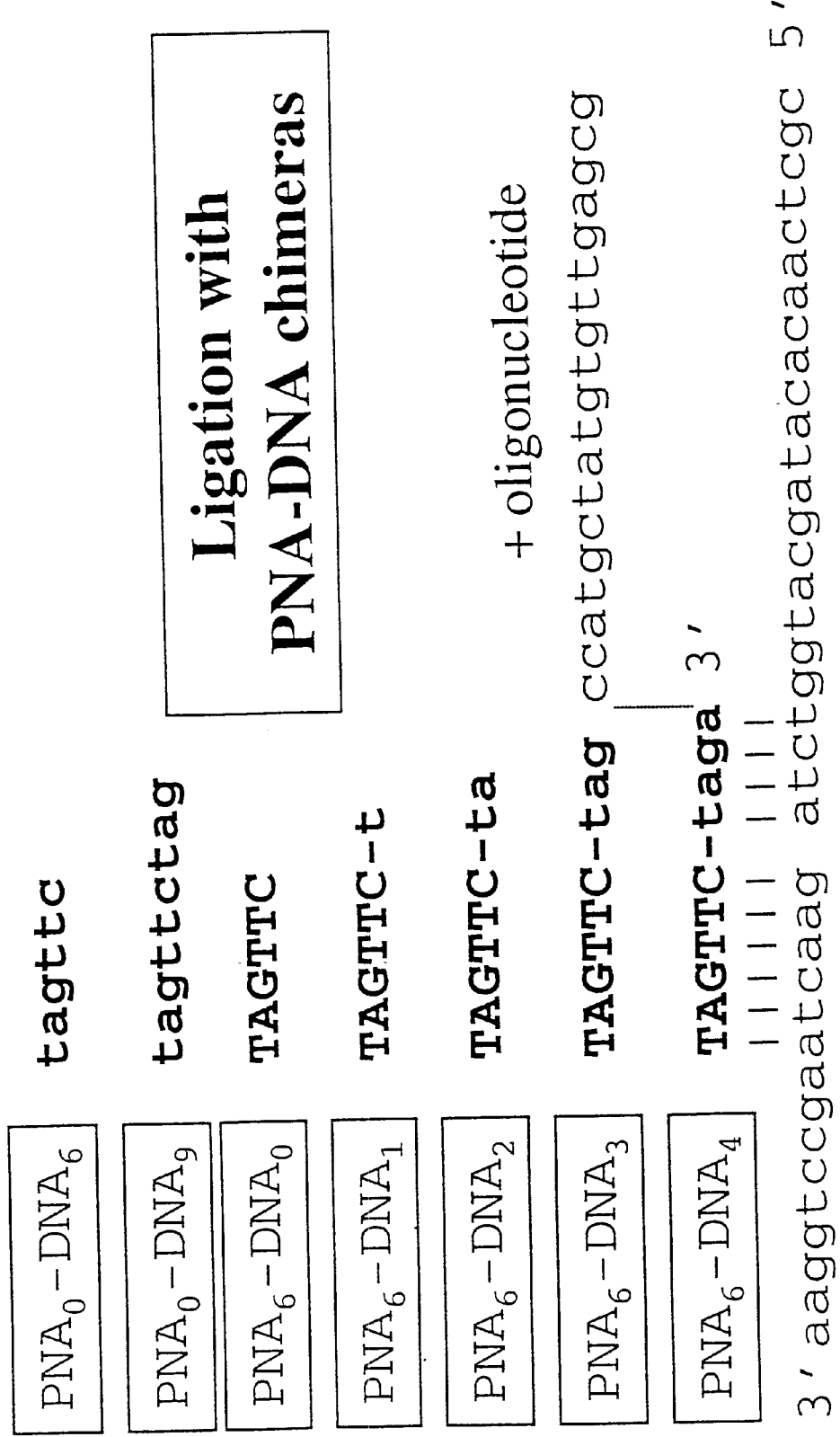

FIGS. 3A–3B Generalized schematic of ligation: (3A) between a 3'-hydroxyl PNA-DNA chimera and a 5'-phosphate oligonucleotide hybridized to a DNA template with DNA ligase to form a PNA-DNA ligation product, and (3B) probe sequences and a 38 nt perfect match DNA template for ligation experiments.

Figure 4A:
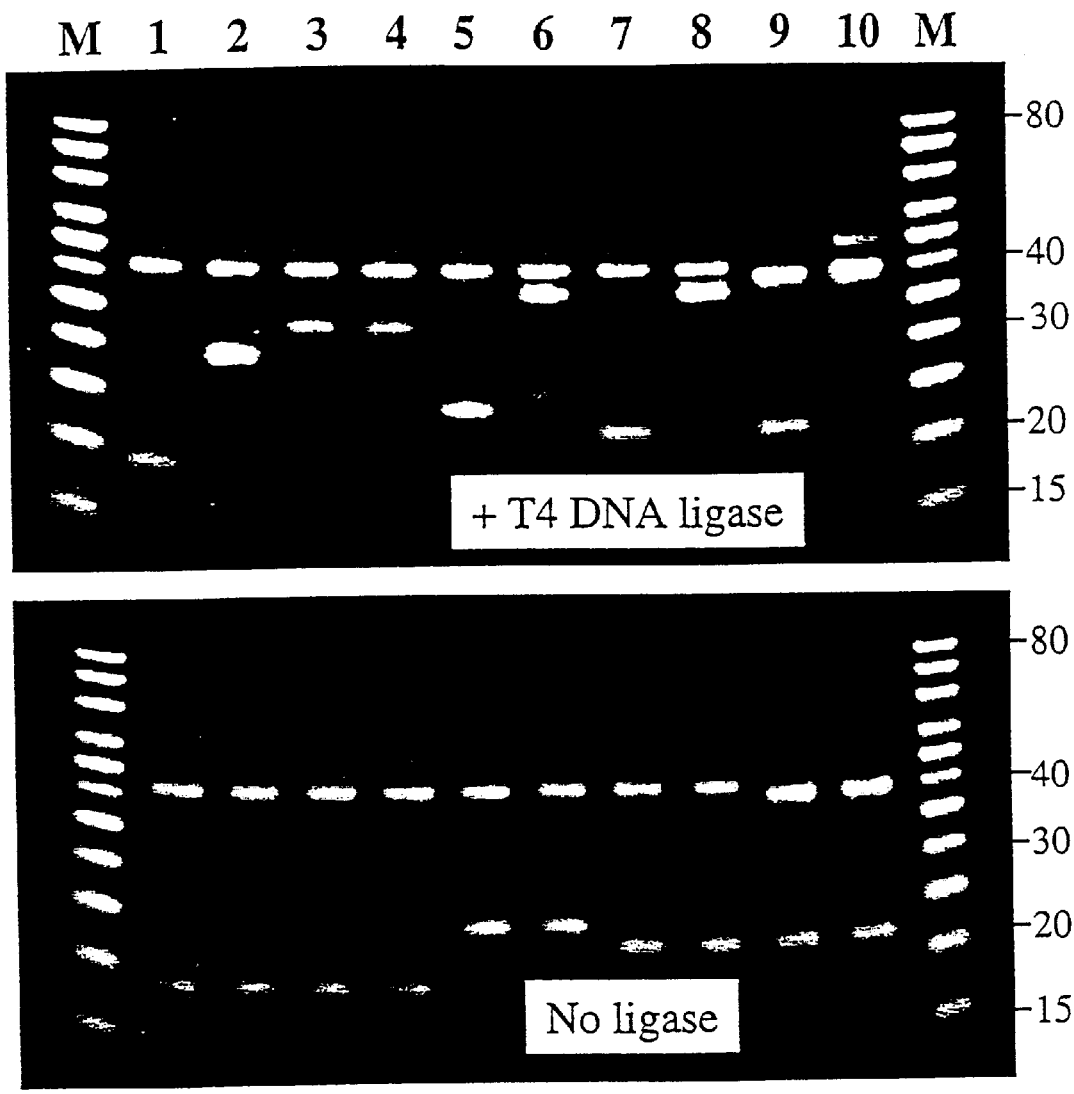
Figure 4A:
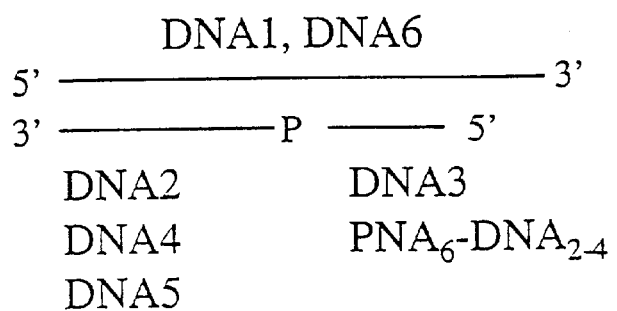
Figure 4B:
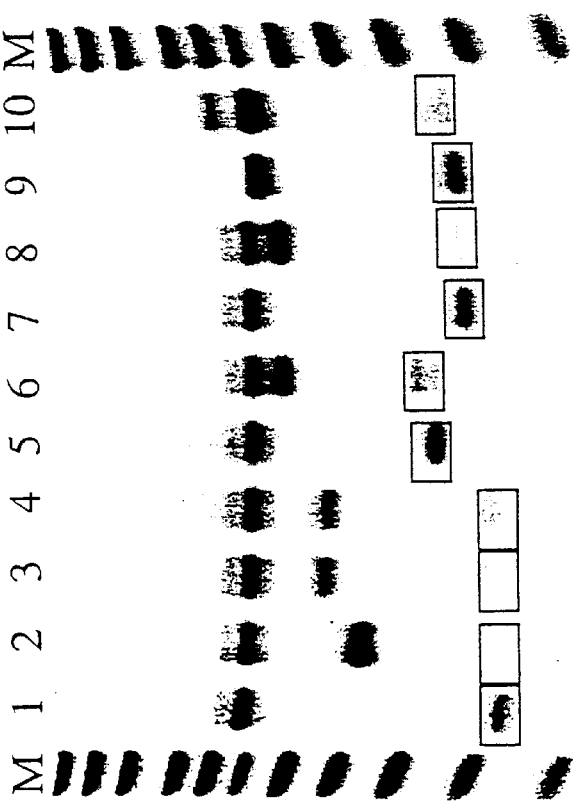

FIGS. 4A–4B Scanned images of PAGE analysis of ligation experiments: (4A top) with T4 DNA ligase and (4A bottom) without ligase; and (4B) quantitative estimate of ligation by densitometry, SpotDenso program.

Figure 5A:
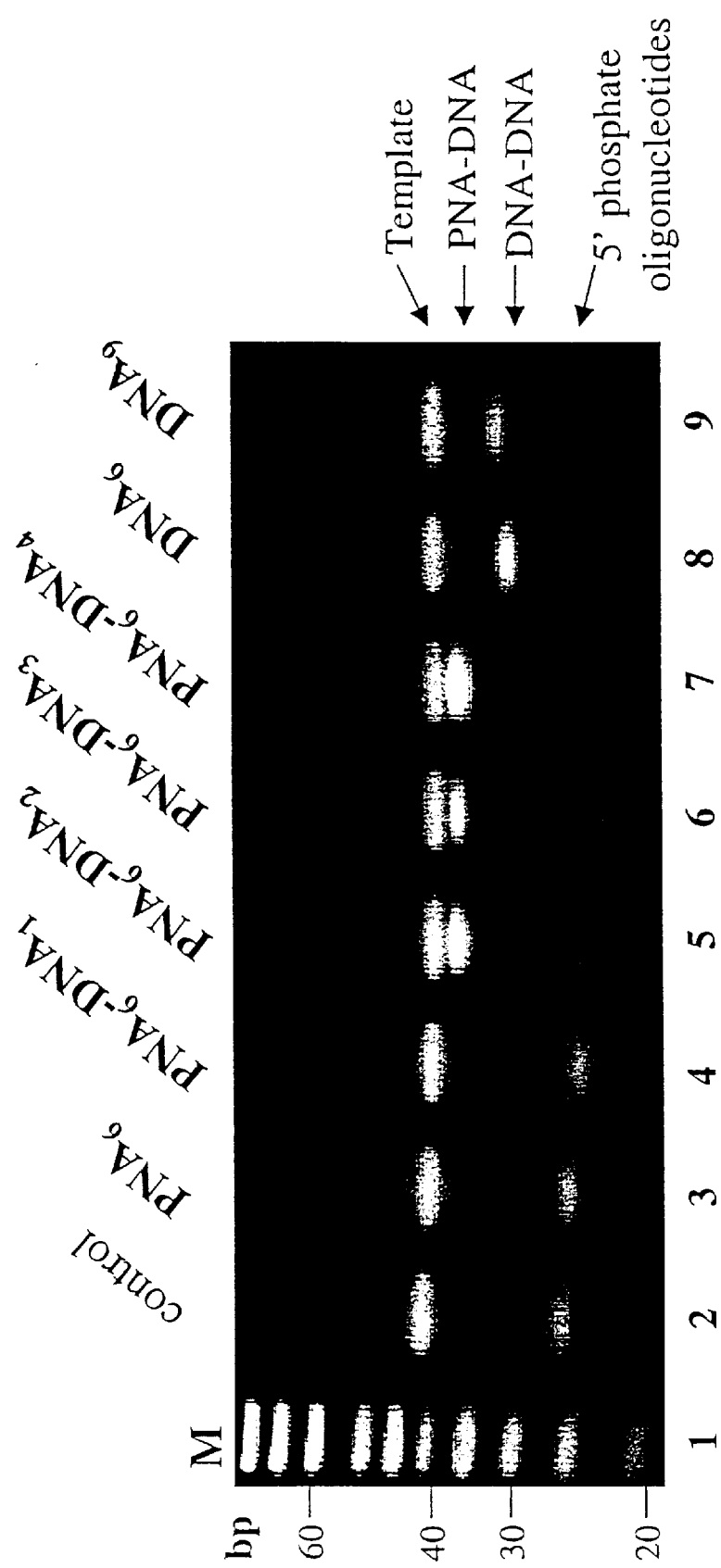
Figure 5B:
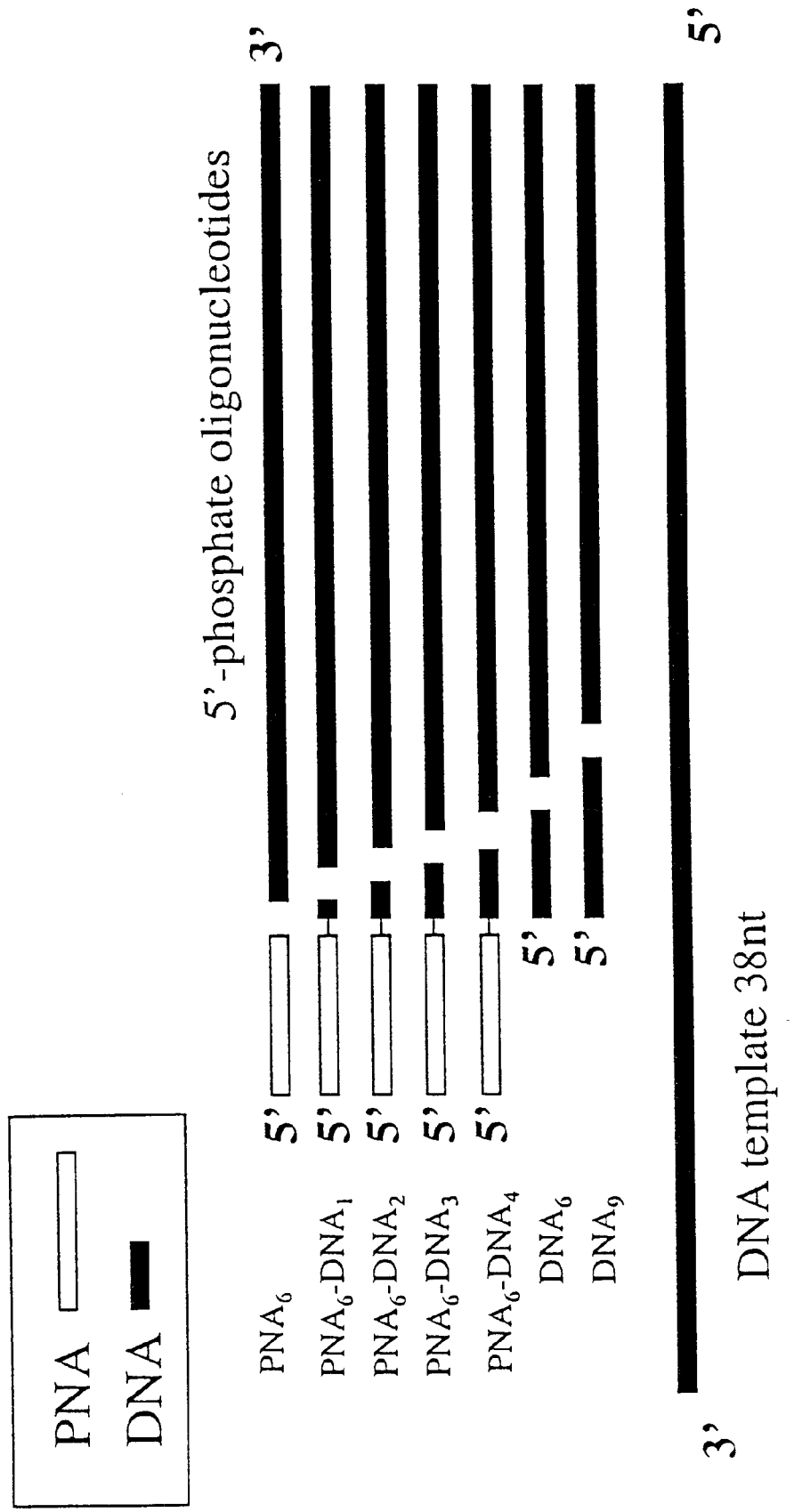

FIGS. 5A–5B Scanned images of PAGE analysis of ligation experiments with T4 DNA ligase: (5A) SYBR-Green stained gel image; and (5B) schematic of ligation of PNA, PNA-DNA chimera, and DNA to 5'-phosphate oligonucleotides hybridized to a DNA template 38 nt.

Figure 6:
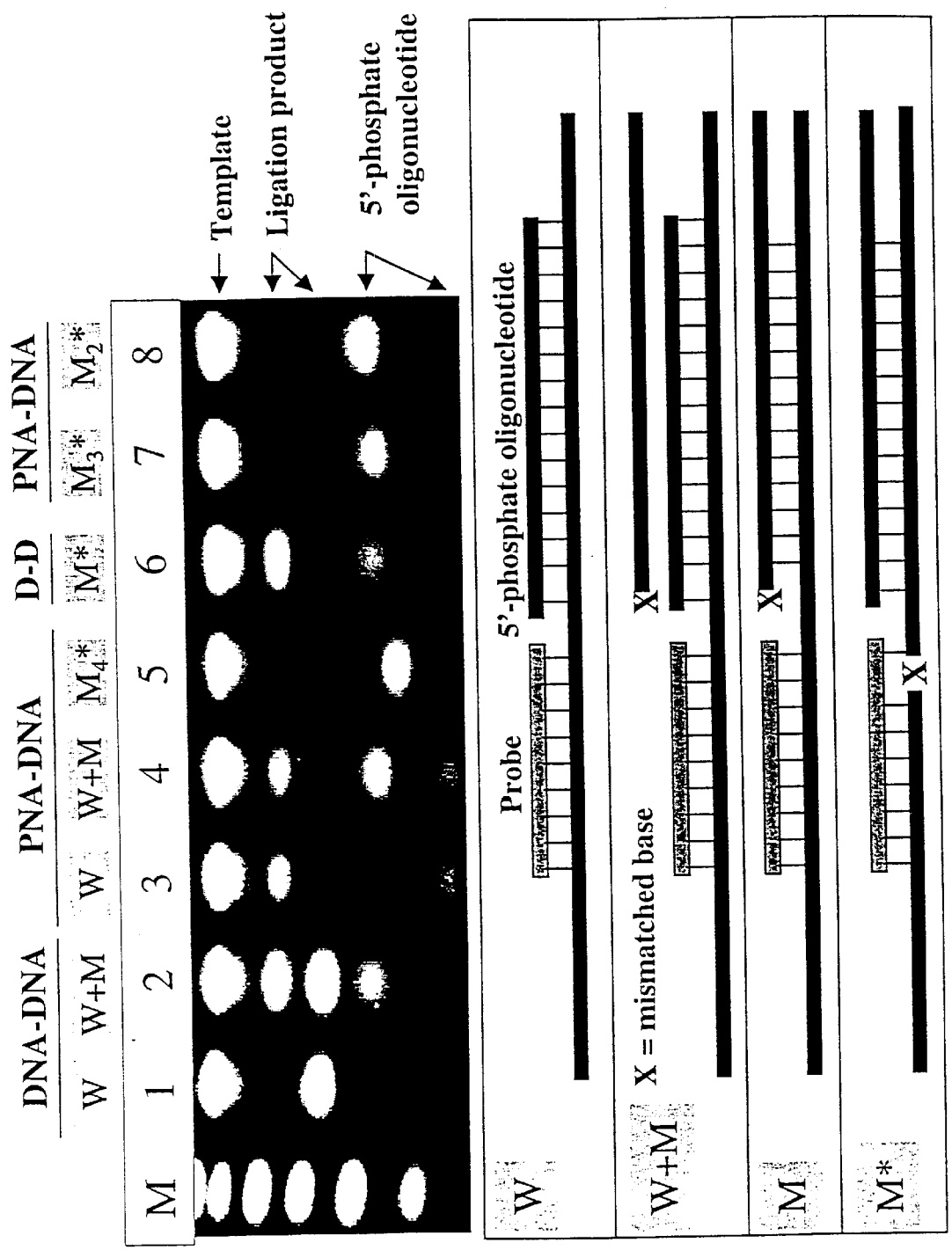

FIG. 6 Scanned image of PAGE analysis of PNA-DNA chimera ligase reactions detecting wild-type and mutant sequences. Specificity of PNA-DNA chimeric probe: oligonucleotide ligation relative to oligonucleotide:oligonucleotide ligation.

Figure 7B:
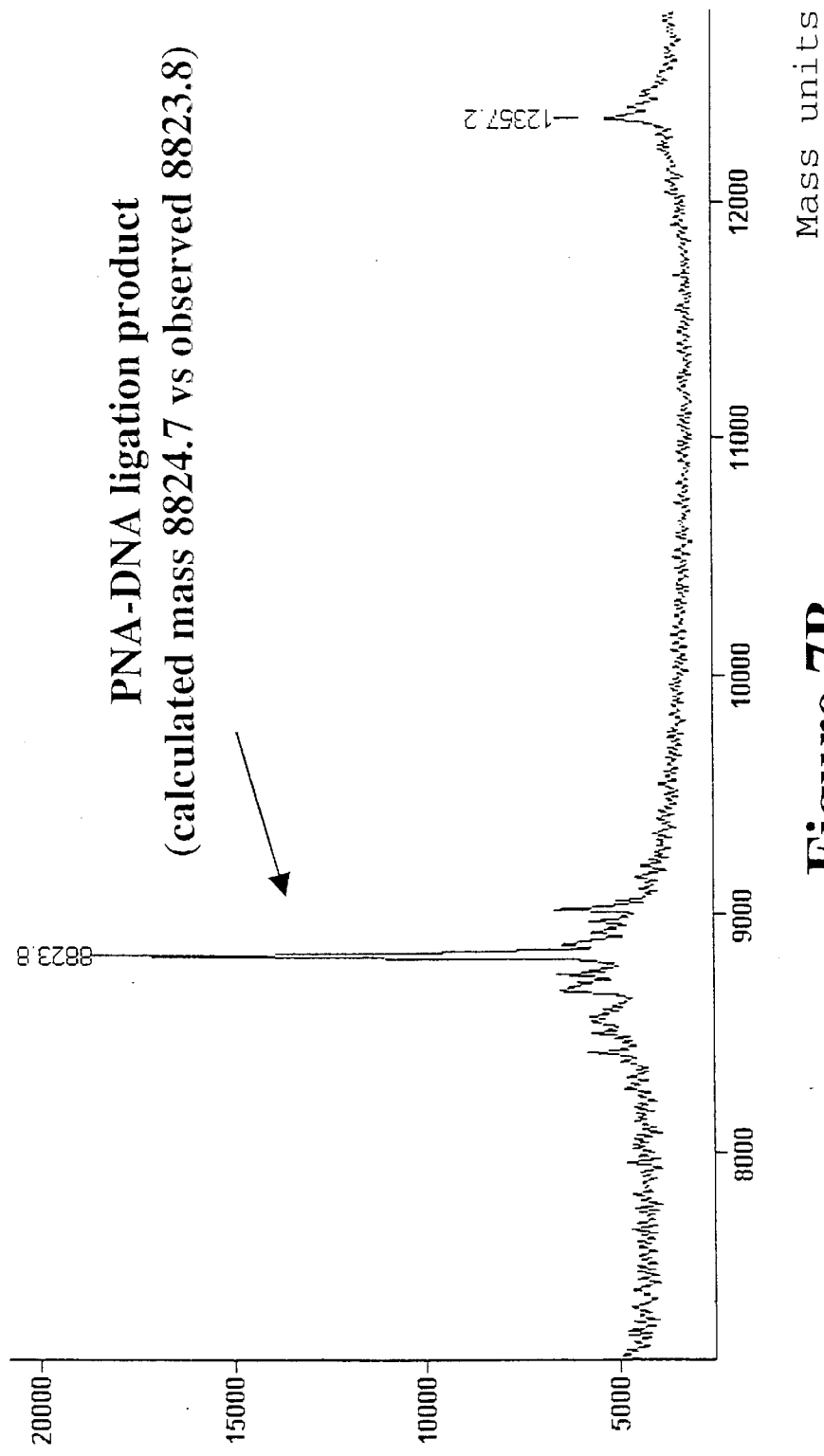

FIGS. 7A–7B MALDI-TOF Mass Spectroscopy analysis of ligation reaction products: (7A) without ligase and (7B) with ligase.

Figure 8A:
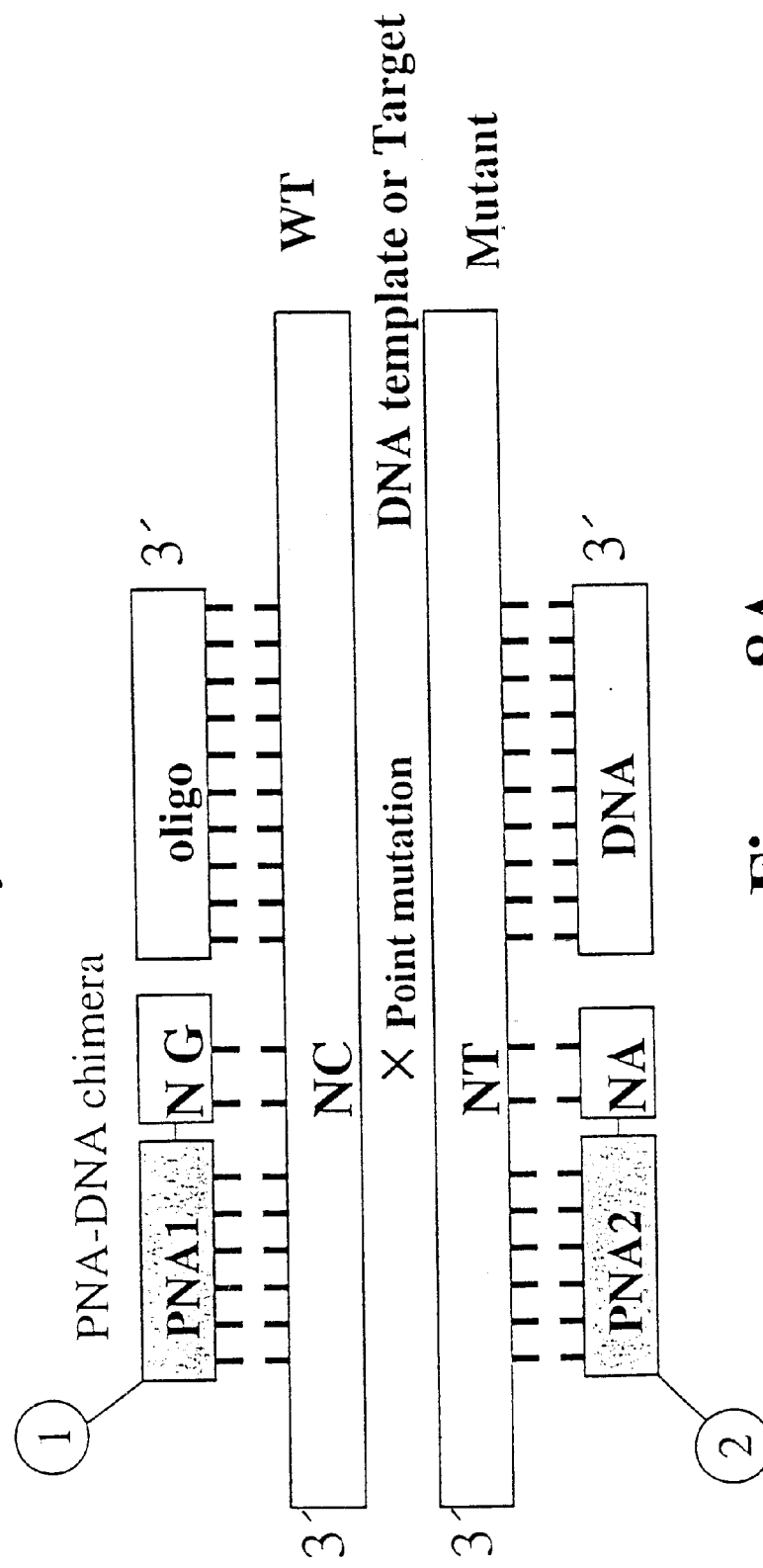
Figure 8B:
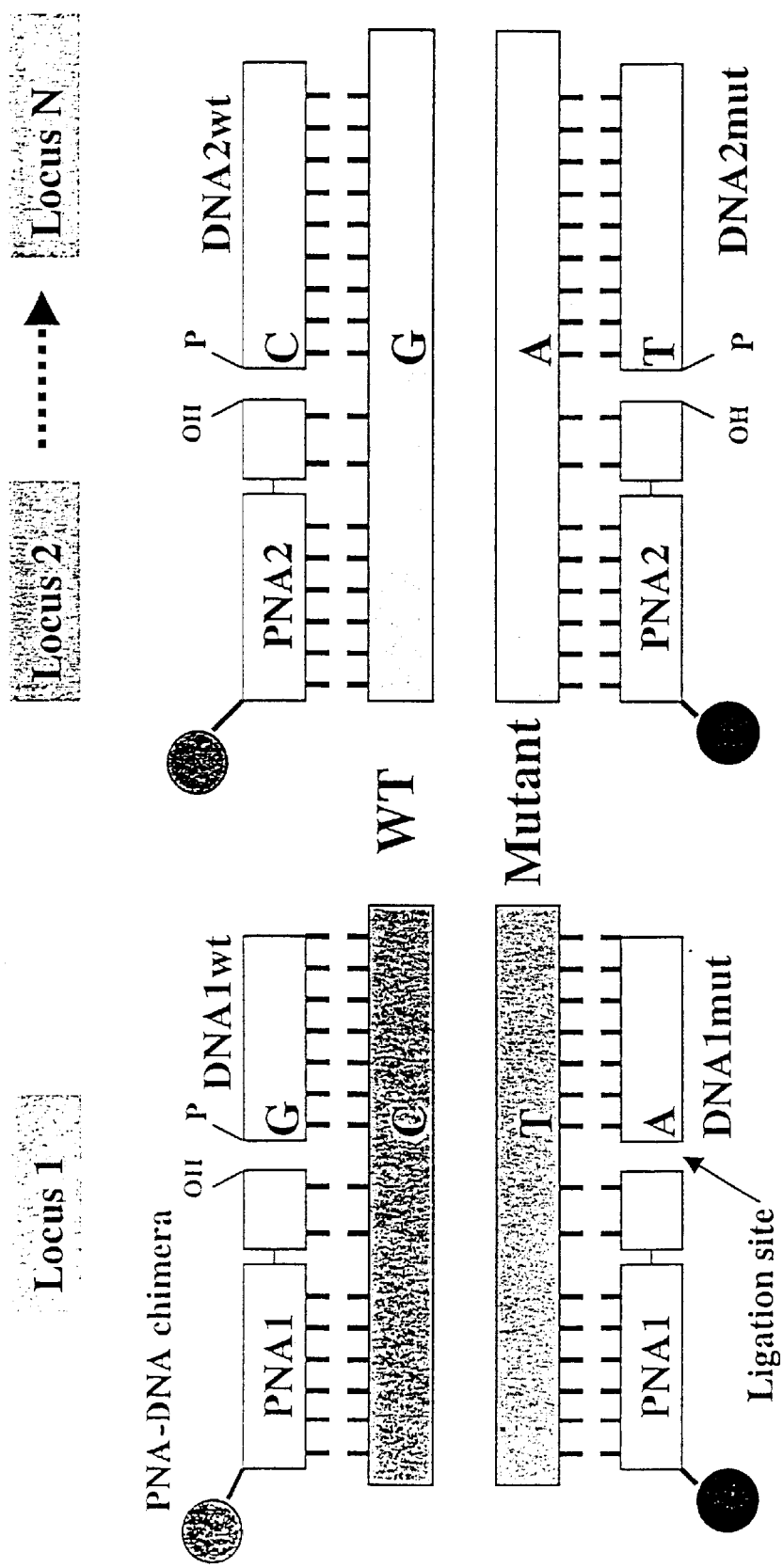

FIGS. 8A–8B Oligonucleotide Ligation Assay (OLA) with PNA-DNA chimeric probes. (8A) Determining the nature of a locus with different dye labels; (8B) Multiplex OLA with mismatched base at 5'-phosphate of oligonucleotides of different lengths and/or mobility modifiers; (8C) Multiplex OLA with mismatched base at 3'terminus of PNA-DNA chimeras of different lengths and/or mobility modifiers FIGS. 9A–9B Oligonucleotide ligation assay with PNA-DNA chimera probes to discriminate mutations in human CFTR loci: (9A) human pCFTR621G-T: exon 4; (9B) human pCFTR1078delT: exon 7; (9C) human pCFTRG551D: exon 11. (UPPER CASE—PNA, lower case—DNA); (9D) OLA with $PNA_{10\ mer}$-$DNA_{3mer}$ at CFTR locus 621G-T. Visualized and recorded under UV illumination (top) and with SYBR Green staining (bottom).

VI. DETAILED DESCRIPTION OF THE PREFERRED EMBODIMENTS

Reference will now be made in detail to the preferred embodiments of the invention. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

VI.1 Definitions

Unless stated otherwise, the following terms and phrases as used herein are intended to have the following meanings:

"Nucleobase" refers to a nitrogen-containing heterocyclic moiety, e.g. a purine, a 7-deazapurine, or a pyrimidine.

Typical nucleobases are adenine, guanine, cytosine, uracil, thymine, 7-deazaadenine, 7-deazaguanine, and the like.

"Nucleoside" refers to a compound consisting of a nucleobase linked to the C-1' carbon of a ribose sugar.

"Nucleotide" refers to a phosphate ester of a nucleoside, as a monomer unit or within a nucleic acid. Nucleotides are sometimes denoted as "NTP", or "dNTP" and "ddNTP" to particularly point out the structural features of the ribose sugar. "Nucleotide 5'-triphosphate" refers to a nucleotide with a triphosphate ester group at the 5'position. The triphosphate ester group may include sulfur substitutions for the various oxygens, e.g. α-thio-nucleotide 5'-triphosphates.

As used herein, the term "nucleic acid" encompasses the terms "oligonucleotide" and "polynucleotide" and means single-stranded and double-stranded polymers of nucleotide monomers, including 2'-deoxyribonucleotides (DNA) and ribonucleotides RNA). The nucleic acid may be composed entirely of deoxyribonucleotides, entirely of ribonucleotides, or chimeric mixtures thereof, linked by internucleotide phosphodiester bond linkages, and associated counterions, e.g., $H^+$, $NH_4^+$, trialkylammonium, $Mg^{2+}$, $Na^+$ and the like. Nucleic acids typically range in size from a few monomeric units, e.g. 5–40 when they are commonly referred to as oligonucleotides, to several thousands of monomeric units. Unless denoted otherwise, whenever an oligonucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted.

The term "Watson/Crick base-pairing" refers to the hydrogen-bonding base pairing commonly observed in double-stranded DNA.

"Attachment site" refers to a site on a moiety, e.g. a chimera or nucleotide, to which is covalently attached a linker.

"Linker" refers to a moiety that links one moiety to another, e.g.: (i) a label to an oligonucleotide or PNA-DNA chimera, or (ii) the PNA moiety to a DNA moiety in a PNA-DNA chimera.

"PNA-DNA Chimera" refers to an oligomer comprised of: (i) a contiguous moiety of PNA monomer units and (ii) a contiguous moiety of nucleotide monomer units with an enzymatically-extendable terminus.

"Alkyl" refers to a saturated or unsaturated, branched, straight-chain, branched, or cyclic hydrocarbon radical derived by the removal of one hydrogen atom from a single carbon atom of a parent alkane, alkene, or alkyne. Typical alkyl groups include, but are not limited to, methyl, ethyl, propyl, butyl, and the like. In preferred embodiments, the alkyl groups consist of 1–12 saturated and/or unsaturated carbons.

"Cycloalkyl" refers to a cyclic alkyl radical. Nitrogen atoms with cycloalkyl substituents may form aziridinyl, azetidinyl, pyrrolidinyl, piperidinyl, larger rings, and substituted forms of heterocycles thereof.

"Alkyldiyl" refers to a saturated or unsaturated, branched, straight chain or cyclic hydrocarbon radical of 1–20 carbon atoms, and having two monovalent radical centers derived by the removal of two hydrogen atoms from the same or two different carbon atoms of a parent alkane, alkene or alkyne. Typical alkyldiyl radicals include, but are not limited to, 1,2-ethyldiyl, 1,3-propyldiyl, 1,4-butyldiyl, and the like.

"Aryldiyl" refers to an unsaturated cyclic or polycyclic hydrocarbon radical of 6–20 carbon atoms having a conjugated resonance electron system and at least two monovalent radical centers derived by the removal of two hydrogen atoms from two different carbon atoms of a parent aryl compound. Typical aryldiyl groups include, but are not limited to, radicals derived from benzene, substituted benzene, naphthalene, anthracene, biphenyl, and the like.

"Label" refers to any non-radioisotopic moiety covalently attached to a chimera or nucleotide that is detectable or imparts a desired functionality or property in the ligation extension product.

"Ligation" is the enzymatic joining by formation of a phosphodiester bond between a PNA-DNA chimeric probe and a second probe oligonucleotide when the chimera and the second probe are hybridized (annealed) adjacently and to a template nucleic acid.

VI.2 PNA-DNA Chimera

In one aspect, the present invention utilizes chimeric probes which contain PNA moieties and DNA moieties. The PNA moieties may be any backbone of acyclic, achiral, and neutral polyamide linkages to which nucleobases are attached. A preferred form of the PNA moiety is a backbone of N-(2-aminoethyl)-glycine, a peptide-like, amide-linked unit (Buchardt, 1992; Nielsen, 1991), as shown below in a partial structure with a carboxyl-terminal amide:

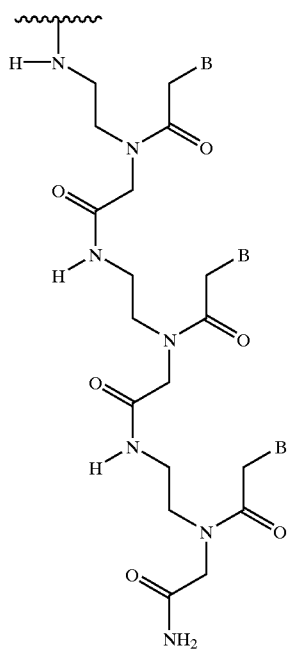

PNA oligomers themselves are not substrates for nucleic acid processing enzymes, such as DNA polymerases (Lutz, 1999; Kyger, 1998; Lutz, 1997).

PNA-DNA chimeras are oligomers comprised of: 1) a contiguous moiety of PNA monomer units and 2) a contiguous moiety of nucleotides. The two moieties are covalently linked together. The nucleotide moiety of the chimera may be 2'-deoxynucleotides, ribonucleotides, or a mixture thereof. The nucleotide moiety of the chimera has a 3' hydroxyl terminus. The preferred length of the PNA moiety is from 3 to 15 PNA monomer units, reflecting optimum enzymatic activity, hybridization specificity and affinity, economy of synthesis reagents, and ease of chimera synthesis and purification. The length of the DNA moiety is from 2 to 15 nucleotides. The preferred length of the DNA moiety is the shortest sequence which promotes efficient ligation, i.e. at least two 2'-deoxynucleotides (FIG. 1A).

Preferred nucleobases in one or more PNA monomer units include, but are not limited to, adenine, guanine, cytosine, uracil, thymine, 7-deazaadenine, 7-deazaguanine, C-5-alkyl pyrimidines, 2-thiopyrimidine, 2,6-diaminopurine, C-5-propyne pyrimidine, phenoxazine (Flanagan, 1999), 7-deazapurine, isocytidine, pseudo-isocytidine (Egholm, 1995), isoguanosine, 4(3 H)-pyrimidone, hypoxanthine, and 8-oxopurines (Meyer, 1994).

The increased affinity and specificity (Egholm, 1993; Jensen, 1997) conferred by the PNA moiety in a PNA-DNA chimera allows for shorter probes to be used in hybridization experiments and assays (Uhlmann and Peyman, 1998; Uhlmann, 1998; Cook; 1997; Uhlmann, 1996. In general, shorter probes are more specific than corresponding longer probes, i.e. the relative structural perturbation is larger in a smaller probe. Also, shorter probes are more economical, i.e. cheaper to synthesize, and require less sequence information to design. It is desirable to provide methods by which PNA-DNA chimeras can be ligated to oligonucleotides and other PNA-DNA chimeras to form PNA-containing ligation products.

Binding of the PNA moiety in a PNA-DNA chimera to its DNA or RNA complement can occur in either a parallel or anti-parallel orientation. The anti-parallel duplex, where the carboxyl terminus of PNA is aligned with the 5' terminus of the complement DNA, and the amino terminus of PNA is aligned with the 3' terminus of the DNA complement, is typically more stable than the parallel duplex, where the carboxyl terminus of PNA is aligned with the 3' terminus of the DNA complement and the amino terminus of PNA is aligned with the 5' terminus of the DNA complement (Koppitz, 1998; Egholm, 1993). The exemplary chimeras shown here are designed such that the PNA moiety anneals in the anti-parallel orientation with the target sequences. Whenever a PNA sequence is represented as a series of letters, it is understood that the amino terminus is at the left side and the carboxyl terminus is at the right side.

Chimera sequences are typically completely complementary to a portion of the target sequence. However, chimera sequences may contain mixed-base ("redundant" or "degenerate") sites whereby a chimera sample may be a mixture of sequences with one or more base positions represented by two or more different nucleobases. The mixed-base site may be located in the PNA or DNA moieties of the oligomer. Mixed-base chimeras are mixtures of sequences with varying levels of complementarity to a particular target sequence. Mixed-base chimeras may be useful for random priming or where template sequence information is unknown or uncertain.

Although certain features of the invention are illustrated herein using single-stranded probes and template nucleic acids, it will also be appreciated that any of the probes and template nucleic acids may contain double-stranded regions. It is also contemplated that PNA-DNA chimeras may undergo ligation as one or both strands of a duplex ligating with a second duplex, where both strands of each duplex may ligate with overhangs ("sticky ends"). For example, the chimeric probe can be provided in double-stranded form with a sticky end such that the overhang strand contains the DNA moiety and at least a portion of the PNA moiety which is complementary to the template nucleic acid, and such that the recessed strand of the chimeric probe, upon hybridization of the chimeric probe to the template, is positioned either immediately adjacent to, or spaced by a gap of one or more nucleotide positions from, a terminal end of the template nucleic acid. Also contemplated are templates containing a PNA moiety of one or more PNA monomers which allow ligation of adjacently hybridized probes.

PNA-DNA chimeras can be synthesized by covalently linking PNA monomers and nucleotides in virtually any combination or sequence, using the respective conventional methods of synthesis of PNA oligomers, DNA oligonucleotides, and RNA oligonucleotides (Vinayak, 1997; Uhlmann, 1996; Van der Laan, 1997). Efficient and automated methods have been developed for synthesizing PNA/DNA chimera at a 2–25 μmole scale on commercially available, automated synthesizers, e.g. "Expedite™", Model 433A and Model 394 Synthesizers (PE Biosystems), and with commercially available reagents (Uhlmann, 1996; Vinayak, 1997; Van der Laan, 1997). In this approach, the chimeras can be made continuously, in a single column and on a single synthesizer.

Typically, synthesis of chimeras is initiated by detritylation of the 5'-dimethoxytrityl (DMT) group of commercially available, high-cross link, non-swelling polystyrene beads packed in a synthesis column. The supports are loaded at 20–30 μmole/g with 5'-DMT deoxynucleosides ($A^{bz}$, $G^{ibu}$, $C^{bz}$, T) linked through the 3' hydroxyl to the support through a base-labile succinate/hydroxymethylbenzoic acid linker (Vinayak, 1997). 5'-DMT, 3'-cyanoethyl phosphoramidite deoxynucleoside monomers (Beaucage, 1992) are dissolved in dry acetonitrile and delivered concurrently with tetrazole activator and coupled to the support-bound 5'-hydroxyl. Coupling is followed by capping with acetic anhydride of unreacted 5'-hydroxyls, and iodine oxidation to the pentavalent internucleotide phosphate triester. The DNA synthesis cycle is repeated until the last deoxynucleoside addition, where a 5' monomethoxytrityl (MMT) amino nucleoside phosphoramidite is employed to furnish a 5' amino terminus on the support-bound DNA moiety, for coupling to a PNA monomer at the linkage between DNA and PNA in the chimera. The MMT group is favored for protection of the backbone amino in the synthesis of PNA-DNA chimeras because of its acid-lability. The MMT group is efficiently and rapidly removed from nitrogen under mild acidic conditions which do not cause depurination or other damage to the chimera.

To initiate synthesis of the PNA moiety, the 5' MMT group is removed with 3% trichloroacetic acid in dichloromethane and the amino group is coupled with a PNA monomer and a coupling reagent. The backbone amino group of the PNA monomers is preferably protected with MMT and the nucleobase exocyclic amines are protected as $A^{bz}$, $G^{ibu}$, and $C^{bz}$ (Breipohl, 1997; Finn, 1996; Will, 1995). Any conventional peptide coupling reagent may be used, but HBTU and HATU are preferred coupling reagents. PNA monomers may be dissolved in 1:1 DMF:acetonitrile to a concentration of about 0.2M. Prior to delivery to the synthesis column, the monomer solution is mixed with an equal volume of 0.2M HBTU (O-benzotriazol-1-yl-N,N,N',N'-tetramethyluronium hexafluorophosphate), also in 1:1 DMF:acetonitrile (Vinayak, 1997). The solution is delivered to the column concurrently with 0.2M diisopropylethylamine in 1:1 DMF:acetonitrile. The synthesis cycles for the PNA and DNA moieties in a chimera on a Model 394 synthesizer at a 2 μmole scale are summarized in Table 1 below.

TABLE 1

PNA-DNA chimera synthesis cycles

| Step | Function | Reagents | PNA Time (sec) | DNA Time (sec) |
|---|---|---|---|---|
| 1 | Detritylation | 3% $CCl_3CO_2H$ in $CH_2Cl_2$ | 60 | 25 |
| 2 | Coupling | PNA: 0.2 M PNA monomer, HBTU, DiPEA in 1:1 DMF:$CH_3CN$ DNA: 0.1 M DNA monomer, 0.5 M tetrazole in $CH_3CN$ | 960 | 25 |
| 3 | Capping | $Ac_2O$, lutidine, N-methylimidazole, THF | 25 | 15 |
| 4 | Oxidation | iodine, pyridine, $H_2O$, THF | not required | 25 |

After synthesis is complete, the amino terminus may be acetylated to minimize migration or cyclization, or reacted as a nucleophile in labelling. The crude chimera is cleaved from the support, and all protecting groups are removed with concentrated ammonium hydroxide at 55° C. for 8–16 hours. The chimeras are analyzed and purified by reverse-phase HPLC or polyacrylamide gel electrophoresis (PAGE), analyzed by mass spectroscopy, and quantified by correlating UV absorbance at 260 nm with mass.

Chimeras with a DNA moiety comprising ribonucleotides can be synthesized with the appropriate RNA phosphoramidite nucleosides and/or 5' DMT protected ribonucleotides support (Vinayak, 1994). The 2' hydroxyl of RNA phosphoramidites are typically protected with the tert-butyldimethylsilyl (TBDMS) group and the exocyclic amino groups of the nucleobases are protected as $A^{bz}$, $G^{dmf}$, $C^{bz}$. After synthesis, TBDMS groups are removed with a fluoride reagent, e.g. tetrabutylammonium fluoride in tetrahydrofuran. Otherwise, the synthesis, purification, and analysis methods for ribonucleotide-containing PNA-DNA chimeras are virtually the same as for chimeras with only 2'-deoxynucleotide containing DNA moieties.

Figure 2A:
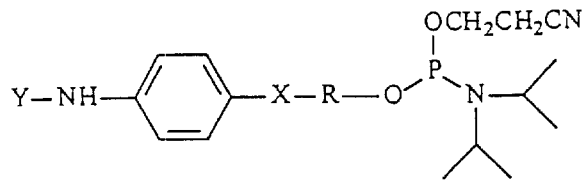

The linkage between the PNA and DNA moieties of the chimeric probes of the invention may be a direct bond, e.g. an amide bond formed by the amino group at the 5' of a deoxynucleotide and the carboxyl group at the carboxyl terminal of the PNA moiety without an intervening atom (FIGS. 1A–1B). Alternatively, the linkage L may be a phosphodiester or phosphoramidate group. The linkage may also comprise one or more units of a non-base pairing moiety such as ethyleneoxy, linked to the PNA and DNA moieties by amide (FIG. 2B) or phosphate (FIG. 2C) bonds. Ethyleneoxy linkage units between the PNA and DNA moieties can be installed by coupling reagents such as protected forms of 2-[2-(2-aminoethoxy) ethoxy] acetic acid. The O-linker, 2-[2-(2-aminoethoxy] acetic acid, is coupled as the MMT-amino protected amide-forming carboxylic acid, or phosphoramidite synthons (FIG. 2A). One or more O linker units can act as a flexible, non-base pairing, linkage between the PNA and DNA moieties. FIG. 2 shows a bis-ethyleneoxy-acetamido linker (2B) and a bis-ethyleneoxy-phosphate linker (2C). Other exemplary linkers include alkydiyl, e.g. hexyldiyl (Vinayak, 1997), or 1,4-phenyldiyl (FIG. 2A).

VI.3 Oligonucleotides

Generally, the oligonucleotides of the present invention are prepared by the phosphoramidite synthesis method, preferred because of its efficient and rapid coupling and the stability of the starting nucleoside monomers (Caruthers, 1983; Beaucage, 1983; Beaucage, 1992). The phosphoramidite method entails cyclical addition of nucleotide monomer units to an oligonucleotide chain growing on a solid-support, most commonly in the 3' to 5' direction in which the 3' terminus nucleoside is attached to the solid-support at the beginning of synthesis. The method is usually practiced using automated, commercially available synthesizers (Caruthers, 1984). Typically, phosphoramidite nucleoside monomer units include:

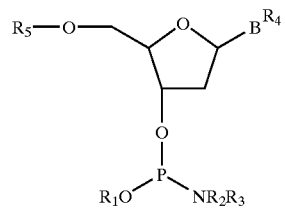

where, $R_1$ is a protecting group or substituent, e.g. cyanoethyl, methyl, lower alkyl, substituted alkyl, phenyl, aryl, and substituted aryl; $R_2$ and $R_3$ are amine substituents, e.g. isopropyl, morpholino, methyl, ethyl, lower alkyl, cycloalkyl, and aryl; $R_4$ is an exocyclic nitrogen protecting group such as benzoyl, isobutyryl, acetyl, phenoxyacetyl, aryloxyacetyl, dimethylformamidine, dialkylformamidine, and dialkylacetamidine; and $R_5$ is an acid-labile protecting group such as DMT, MMT, pixyl, trityl, and trialkylsilyl.

Preferred nucleobases in one or more nucleosides include, but are not limited to, adenine, guanine, cytosine, uracil, thymine, 7-deazaadenine, 7-deazaguanine, C-5-alkyl pyrimidines, 2-thiopyrimidine, 2,6-diaminopurine, C-5-propyne pyrimidine, phenoxazine (Flanagan, 1999), 7-deazapurine, isocytidine, pseudo-isocytidine (Egholm, 1995), isoguanosine, 4(3 H)-pyrimidone, hypoxanthine, and 8-oxopurines (Meyer, 1994).

Preferred sugars in one or more of the nucleosides include, but are not limited to, 2'-deoxyribose, ribose, and 2'- or 3'-ribose modifications where the 2'- or 3'-position may be hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo.

Other preferred sugars include 4'-α-anomeric nucleotides, 1'-α-anomeric nucleotides, and 2'-4'-linked and other "locked", bicyclic sugar modifications (Wengel, 1999).

VI.4 Ligase Enzymes

The ligase enzyme used in the present invention can be any ligase that performs ligation of the PNA-DNA chimeric probe to the second probe, when the chimeric probe and second probe are annealed to adjacent regions in a target template. DNA ligases join DNA sequences by forming a phosphodiester bond between a 5'-phosphate and a 3'-hydroxyl on two probes which are adjacent, i.e. hybridized immediately next to each other (Kornberg, 1980; Whiteley, 1989). Alternatively, the 3'-phosphate end of one probe and the 5'-hydroxyl of the other probe may form a phosphodiester bond. In the present invention, one or both probes contain a PNA moiety.

For example, the DNA ligase from bacteriophage T4 can join both DNA and RNA sequences, and it can use either DNA or RNA templates to align the sequences to be ligated. Reactions involving only DNA strands proceed with greater efficiency. Two DNA duplexes with base-paired blunt ends can be joined by the phage ligase. Certain ligases need cofactors such as NAD or ATP.

A number of ligases have recently been isolated from thermophile organisms and which have significant activity above 60° C. and survive conditions that denature DNA. A preferred thermostable ligase is derived from *Thermus aquaticus* (Takahashi, 1984) and can also be prepared recombinantly (Barany, WO 91/17239, 1991). The thermostable ligases also exhibit a reduced activity of joining duplex DNA with blunt ends or short complementary overhang ends. These properties result in increased specificity of detection and convenience in many analytical assays and applications involving ligation.

VI.5 Labels

It is desirable to provide methods by which labelled PNA-DNA chimeras and labelled oligonucleotides can be enzymatically ligated as probes to form non-radioisotopically labelled ligation products. Fluorescence has largely supplanted radioactivity as the preferred detection method for many ligation experiments and applications, such as the oligonucleotide ligation assay and other in vitro DNA probe-based diagnostic tests. Therefore, fluorescent labels are a preferred class of detection labels. Labels which enhance hybridization specificity and affinity are also preferred, e.g. minor-groove binders. Affinity ligand labels are also preferred. Biotin is a useful affinity ligand label for chimeric probes and oligonucleotides for capture and isolation of ligation products. In certain experiments, biotin labelling of the template nucleic acid may be useful for capture, isolation, removal, or retrieval purposes.

The PNA-DNA chimeras and the oligonucleotides participating in ligation may bear covalently attached labels. Labeling can be accomplished using any one of a large number of known techniques employing known labels, linkages, linking groups, standard reagents and reaction conditions, and analysis and purification methods. Generally, the linkage linking the dye and oligonucleotide or chimera should not (i) interfere with ligation, (ii) inhibit ligase activity, or (iii) adversely affect the fluorescence properties of the dye, e.g. quenching or bleaching.

PNA-DNA chimeras and oligonucleotides can be labelled at sites including a nucleobase, a sugar, the aminoethylglycine backbone, amino, sulfide, hydroxyl, and carboxyl. Nucleobase label sites generally include the 7-deaza or C-8 positions of the purine or deazapurine, and the C-5 position of the pyrimidine. The linkage between the label and the chimera or oligonucleotide (NUC) may be acetylenic-amido or alkenic-amido linkages (Khan, 1998). Typically, a carboxyl group on the label is activated by forming an active ester, e.g. N-hydroxysuccinimide (NHS) ester and reacted with an amino group on the alkynylamino- or alkenylamino-derivatized chimera or nucleotide. The resulting linkage is 3-(carboxy)amino-1-propyn-1-yl having the structures:

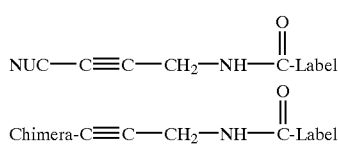

Labels may be attached to oligonucleotides at any suitable terminal or internal attachment sites, including: (i) a terminus, e.g. 5' and/or 3' (Mullah, 1998), (ii) an internucleotide linkage, (iii) a sugar, or (iv) a nucleobase. Labels are most conveniently and efficiently introduced at the 5' terminus with fluorescent dyes (FAM, HEX, TET) and other labels which have been functionalized as phosphoramidite reagents, as part of the automated protocol (Theisen, 1992).

A preferred class of labels provide a signal for detection of the labelled oligonucleotide by fluorescence, chemiluminescence, and electrochemical luminescence (Kricka, 1992). Fluorescent dyes useful for labelling oligonucleotides include fluoresceins (Menchen, 1993), rhodamines (Bergot, 1994), energy-transfer dyes (Lee and Spurgeon, 1998), cyanines (Kubista, 1997), and metal porphyrin complexes (Stanton, 1988).

Examples of fluorescein dyes include 6-carboxyfluorescein (6-FAM), 2',4', 1,4,-tetrachlorofluorescein (TET), 2', 4', 5', 7', 1,4-hexachlorofluorescein (HEX), 2',7'-dimethoxy-4', 5'-dichloro-6-carboxyrhodamine (JOE), and aromatic-substituted xanthene dyes (Benson, 1997). The 5-carboxyl, and other regio-isomers, may also have useful detection properties.

Another preferred class of labels include fluorescence quenchers. The emission spectra of a quencher overlaps with a proximal intramolecular or intermolecular fluorescent dye such that the fluorescence of the fluorescent dye is substantially diminished, or quenched, by the phenomenon of fluorescence resonance energy transfer "FRET" (Clegg, 1992). An example of FRET in the present invention is where the PNA-DNA chimeric probe is labelled with a fluorescent dye and the second probe is labelled with a fluorescence quencher. Alternatively, the chimera may be labelled with a fluorescent quencher and the second probe is labelled with a fluorescent dye. Prior to hybridization and ligation, the fluorescent dye is substantially unquenched. After ligation, the fluorescent dye of the ligation product is substantially quenched by FRET.

Particularly preferred quenchers include but are not limited to (i) rhodamine dyes selected from the group consisting of tetramethyl-6-carboxyrhodamine (TAMRA), tetrapropano-6-carboxyrhodamine (ROX), and (ii) DABSYL, DABCYL, cyanine dyes including nitrothiazole blue (NTB), anthraquinone, malachite green, nitrothiazole, and nitroimidazole compounds and the like. Nitro-substituted forms of quenchers are especially preferred.

Energy-transfer dyes are a preferred class of chimera and oligonucleotide labels. An energy-transfer dye label includes a donor dye linked to an acceptor dye (Lee and Spurgeon, 1998). Light, e.g. from a laser, at a first wavelength is absorbed by a donor dye, e.g. FAM. The donor dye emits excitation energy absorbed by the acceptor dye. The acceptor dye fluoresces at a second, longer wavelength. The donor dye and acceptor dye moieties of an energy-transfer label may be attached by a linker linking the 4' or 5' positions of the donor dye, e.g. FAM, and a 5- or 6-carboxyl group of the acceptor dye. Other rigid and non-rigid linkers may be useful.

Metal porphyrin complexes, e.g. aluminum phthalocyanine tetrasulfonate (Stanton, 1988) and chemiluminescent compounds. e.g. 1,2-dioxetane chemiluminescent moieties (Bronstein, 1990) are also preferred classes of chimera and oligonucleotide labels.

Another preferred class of labels, referred to herein as hybridization-stabilizing moieties, include but are not limited to minor groove binders (Blackburn, 1996, p.337–46), intercalators, polycations, such as poly-lysine and spermine, and cross-linking functional groups. Hybridization-stabilizing moieties may increase the stability of base-pairing, i.e. affinity, or the rate of hybridization, exemplified by high thermal melting temperatures, Tm, of the duplex. Hybridization-stabilizing moieties may also increase the specificity of base-pairing, exemplified by large differences in Tm between perfectly complementary oligonucleotide and target sequences and where the resulting duplex contains one or more mismatches of Watson/Crick base-pairing (Blackburn, 1996, pp. 15–81). Preferred minor groove binders include Hoechst 33258 (Rajur, 1997), $CDPI_{1-3}$ (Kutyavin, 1996), netropsin, and distamycin. Other useful labels include electrophoretic mobility modifiers, amino acids, peptides, enzymes, and affinity ligands, e.g. biotin and digoxigenin.

Linkers between a label and the PNA/DNA chimera can be an amide bond, e.g. where the active ester form of a label is coupled with an amino group of the chimera. Also, linkers can comprise alkyldiyl, aryldiyl, or one or more ethyleneoxy units (Rajur, 1997).

VI.6 Ligation

FIG. 3A shows a generalized schematic of ligation between a 3'-hydroxyl PNA-DNA chimera probe and a 5'-phosphate oligonucleotide, as the second probe, hybridized to a DNA template with DNA ligase to form a PNA-DNA ligation product. The first probe has a 3'-hydroxyl terminus and the second probe has a 5'-phosphate terminus. Alternatively, the first probe has a 5'-phosphate terminus and the second probe has a 3'-hydroxyl terminus.

A ligation mixture generally includes a DNA template, a PNA-DNA chimeric probe, a second probe which is another PNA-DNA chimeric probe or an oligonucleotide, ligase, and other ligation reagents. DNA probes corresponding to the PNA-DNA chimeras may be used as a control or comparison. Under typical conditions, the probes are used at a final concentration of about 1 $\mu$M each.

Additionally, the ligation mixture may contain reagents such as 1×T4 DNA ligase buffer [50 mM Tris-HCl, pH 7.5, 10 mM $MgCl_2$, 10 mM dithiothreitol, 1 mM ATP, 25 $\mu$g/ml bovine serum albumin], and 1,000 units of T4 DNA ligase plus 10 units of T4 polynucleotide kinase in a volume of 50 $\mu$l. The ligation reagent may also contain ligase co-factors, e.g. NAD and ATP, polyethylene glycol, EDTA, KCl, ammonium sulfate, dithiothreitol, BSA, $MgCl_2$, Tris-HCl, glycerol, water, NaCl, mercaptoethanol, and other salts or buffers. The mixture may be incubated at 22 to 25° C. for 3 hours or more. During the ligation, another addition of 10 to 20 units of T4 polynucleotide kinase may be helpful for the ligation.

Typically after incubation, ligase reaction products are heat-inactivated at approximately 80° C. for about 20 minutes and placed on ice or at 4° C. for a short period. For analysis, typically, 5 to 25 pmol of the ligation product is mixed with a final concentration of 1×loading buffer (45 mM Tris base, 45 mM boric acid, 0.4 mM EDTA, 3% Ficoll, 0.02% bromophenol blue, 0.02% xylene cyanol) and denatured at 95° C. for 10 to 20 min. The sample is loaded into a 10 to 15% denaturing PAGE gel and run in 1×TBE (89 mM Tris base, 89 mM boric acid, 2 mM EDTA, pH 8.3) at 100 to 160 V, 70° C. for 25 to 60 min. The ligation product is visualized by staining the gel with SYBR-Green (Molecular Probes, Eugene, Oreg.) in a volume of 40 to 120 ml in 1× TBE for 10 to 30 min. The image may be captured in a gel documentation system (e.g. ChemiImager 4000 Imaging System, Alpha Innotech Corporation, San Leandro, Calif.).

FIG. 3B shows template and probe sequences for a ligation assay in a model system. The probe sequences include two oligonucleotide probes, 6 nt and 9nt, and five PNA-DNA chimeras containing 0 to 4 DNA 2'-deoxynucleotides. The oligonucleotides and chimeras hybridize to a 38 nt DNA template. The template is labelled with biotin at the 3' or 5' end to facilitate isolation and transfer.

Figure 8C:
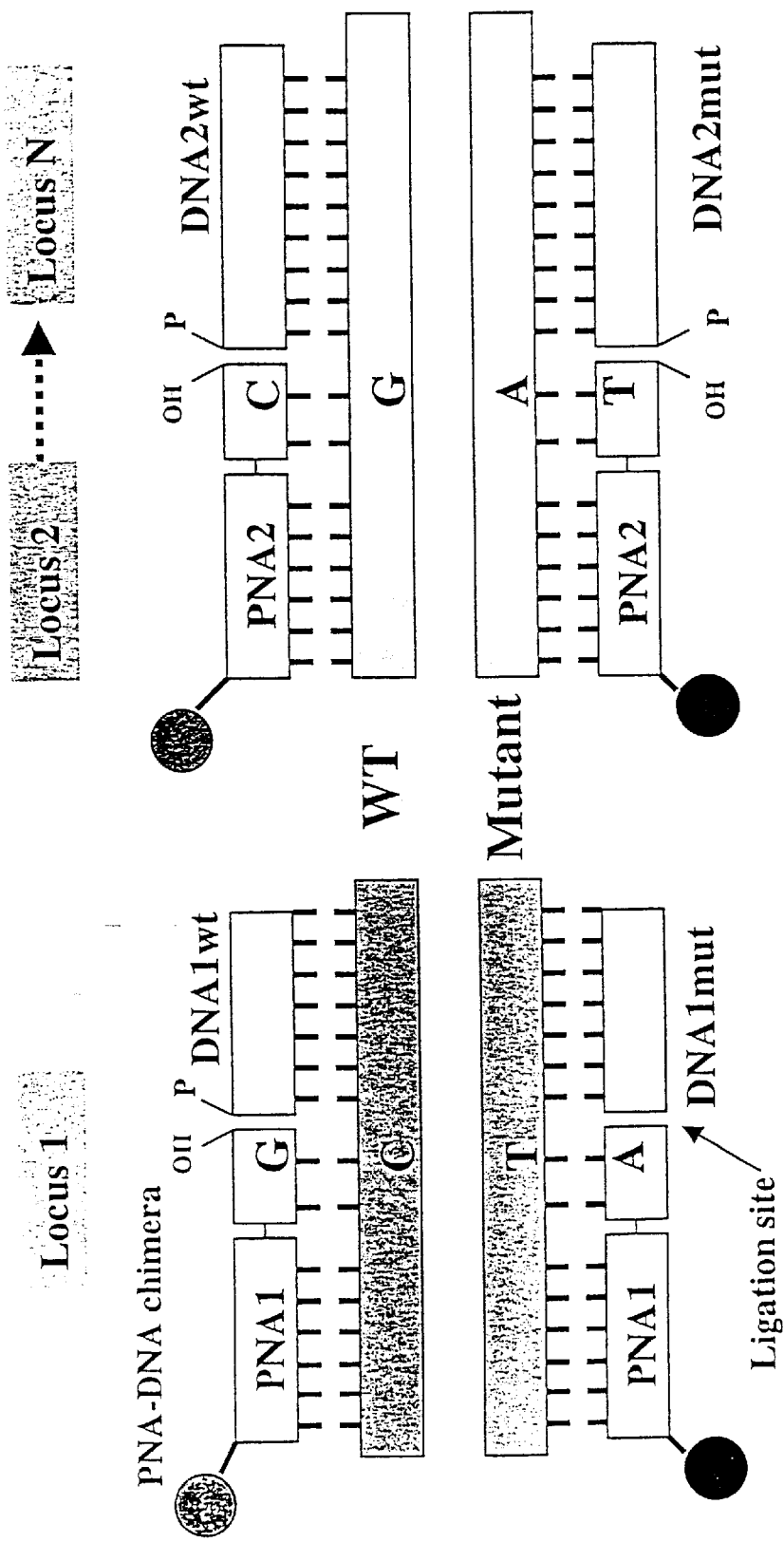

The oligonucleotide ligation assay (OLA) is a convenient, highly-stringent method that permits distinction among known DNA sequence variants (Landegren, 1988). Multiplex analysis of highly polymorphic loci is useful for identification of individuals, e.g., for paternity testing and in forensic science; organ transplant donor-receiver matching, genetic disease diagnosis, prognosis, and pre-natal counseling, and other genetic-based testing which depend on the discrimination of single-base differences at a multiplicity of loci (Delahunty, 1996). Products of a multiplex oligonucleotide ligation assay (OLA) may be resolved electrophoretically from one another and from unligated probes under denaturing conditions with fluorescence detection (Grossman, 1994). For example, FIGS. 8A–8C shows different assays where two PNA-DNA chimeras, a wild-type (WT) sequence chimera and a mutant sequence chimera, bear different fluorescent dyes. Only when the mutant sequence is present in the target sample, will the mutant sequence chimera ligate to the adjacently annealed second probe (oligo) if the mutant base pair is at the ligation site (FIG. 8A).

The ligation products may be discriminated by separation based on: (i) size using electrophoresis or chromatography and/or (ii) detectable labels (Grossman, 1994). With a plurality of fluorescent dyes labelled to chimeras with sequences targetting unique target sequences, multiplexed OLA can be conducted on a single sample in a single vessel. Requirements for efficient multiplex OLA include probes that anneal and ligate in a highly specific and rapid manner. The chimeras and second probe sequences may be selected such that the mutant base, or single base polymorphism, may be at the 5'-phosphate of the second probe (FIG. 8B) or the 3'-terminus of the chimera (FIG. 8C).

It is contemplated that OLA experiments of the present invention may be conducted on solid substrates where the template nucleic acid, PNA-DNA chimeric probe, or the second probe may be immobilized on a solid particle or bead, or a solid porous or non-porous surface. When immobilized, the template, chimera or second probe is preferably covalently attached to the solid substrate, e.g. via a terminal monomer unit. The solid substrate may be polystyrene, controlled-pore-glass, silica gel, silica, polyacrylamide, magnetic beads, polyacrylate, hydroxyethylmethacrylate, polyamide, polyethylene, polyethyleneoxy, and copolymers and grafts of any of the above solid substrates. The configuration or format of the solid substrate may be small particles or beads of approximately 1 to 50 $\mu$m in diameter, membranes, frits, slides, plates, micromachined chips, alkanethiol-gold layers, non-porous surfaces, and polynucleotide-immobilizing media.

For example, a PNA-DNA chimeric probe is covalently attached by a linker at the amino terminus to a non-porous, inorganic surface, e.g. glass (Guo, 1994). A template nucleic acid sample is allowed to hybridized to the chimeric probe under conditions that promote hybridization. A second probe with a sequence complementary to the template is added to the hybridized duplex and the second probe hybridizes to the template adjacent to the chimeric probe. The chimeric probe and second probe are ligated together with ligase. The ligated product may be detected and/or isolated where the chimeric probe, template, or second probe bear a label or affinity ligand and an oligonucleotide ligation assay is thereby performed.

In a preferred embodiment, an array of chimeric probes are assembled on a solid substrate where a chimeric probe of known sequence occupies a defined area on a two-dimensional surface. The number of chimeric probes on any particular surface may be hundreds or even thousands, limited by the spatial requirements for synthesis, attachments, and detection (Fodor, 1995). Alternatively an array of probes may be immobilized on beads or particles contained in wells or vessels. A template, or mixture of templates, may be added for hybridization to the immobilized chimeric probes on the surface. Where sufficient sequence complementarity exists under the defined hybridization conditions, duplex formation will occur. A mixture of second probes may be added separately, or with the template sample, for hybridization. In the presence of ligase, ligation will occur only where chimeric probes and second probes are hybridized adjacently. Unhybridized probes and template samples may be removed by washing under conditions that maintain hybridization, or under denaturing conditions. Where the second probe bears a label, e.g. fluorescent dye, the ligation product is covalently immobilized on the surface and can be detected, e.g. laser-induced fluorescence. From the knowledge of the immobilized chimeric probe sequences, the presence of certain sequences in the template sample can be deduced from the location(s) of detected fluorescence on the array surface.

In a second aspect of the invention, a kit for ligation is provided. In one embodiment, for example, the kit, which is useful for practicing the method of the invention, comprises: (i) a PNA-DNA chimera having from 3 to 15 contiguous PNA monomer units, from 2 to 15 contiguous nucleotides, and a 3' hydroxyl; (ii) a second probe where the second probe is a PNA-DNA chimera or an oligonucleotide and; (iii) a ligase enzyme. The chimera and/or the oligonucleotide may be labelled with a non-radioisotopic label. In another embodiment, the kit additionally includes a template comprising a sequence complementary to the chimera or containing one or more mismatches to the chimera. In another embodiment, the kit additionally includes a polynucleotide kinase.

From the foregoing discussion, it can be seen how various features and advantages of the invention are met. The present invention provides a method for detecting selected target sequences that is highly sensitive and accurate. Selected target sequences can be detected using chimeric PNA/DNA probes containing target-specific sequences shorter than all-DNA probes used in previous oligonucleotide ligation assays. The chimeric probes thus require less target sequence information to design and can be less expensive to synthesize. In addition, the present invention can be adapted to a wide variety of target sequences and assay formats, and can be readily automated.

VI.7 EXAMPLES

The invention is further illustrated by the following examples, which are intended to be purely exemplary of the present invention and not to limit its scope in any way.

Example 1
Labelling of PNA-DNA Chimera
TAMRA and NTB Labelling

Labelling is performed with 5 mg of NHS ester of TAMRA or NTB dissolved in 100 μl DMF or NMP and 10 μl DIEA. The labelling mixture is added to the support bound PNA-DNA chimera and allowed to react for 2 to 18 hours (typically overnight). The support is washed following the labelling with DMF and subsequently DCM prior to cleavage.

CDPI Labelling $CDPI_3$ is attached to the chimera by three consecutive couplings of Fmoc-CDPI (Lukhtanov, 1995) to the amino terminus of a PNA-DNA chimera to give $CDPI_3$-labelled PNA-DNA chimera. The CDPI monomer unit, 1,2-dihydro-(3H)-pyrrolo[3,2-e]indole-7-carboxylate, protected with Fmoc (5 mg, 0.012 mmole) is dissolved in 100 μl NMP and activated by 0.95 equivalents HATU (0.2M in DMF) and 2 equivalents DIEA (0.4M in DMF). After one hour at room temperature, the activated Fmoc-CDPI solution is added to the support bound chimera and allowed to couple for another hour at room temperature. The resin is washed following the coupling with 20 ml DMF. The Fmoc is removed by treatment of the resin support with 1:4 piperidine:DMF for 10 minutes at room temperature. This coupling and deprotection cycle is repeated two additional times for a total of 3 manual couplings to give $CDPI_3$-labelled PNA-DNA chimera.

Example 2
Ligation

FIG. 4 shows ligation experiments where a ligation mixture contained a template and two probes at a final concentration of 1 μM each, 1×T4 DNA ligase buffer [50 mM Tris-HCl, pH 7.5, 10 mM $MgCl_2$, 10 mM dithiothreitol, 1 mM ATP, 25 μg/ml bovine serum albumin], and 1,000 units T4 DNA ligase (New England BioLabs, Beverly, Mass.) in a volume of 50 μl. T4 ligase can also be purchased from Boehringer-Mannheim. Approximately 70 units of NE Biolabs T4 DNA ligase is equal to 1 Weiss unit of Boehringer-Mannheim T4 ligase. The same reactions were also conducted without ligase. After incubation at 22.5 to 25° C. for 3 to 4 hours, the reaction mixture was heated at 80° C. for 20 min. and then stored at 4° C. Five μl of the reaction mixture was analyzed by (15%) polyacrylamide gel electrophoresis (PAGE) under denaturing conditions (7M urea) at 120–140 V for 20–60 min (FIG. 4A). Ligation of 5'-phosphate oligonucleotides (DNA2, DNA4 or DNA5) to an oligonucleotide DNA3 or PNA-DNA chimeras were conducted on templates (DNA1 or DNA6) according to Table 2. Ligation with T4 ligase (top gel image) is evident in lanes 3,4,6,8,10 between PNA-DNA chimeras and 5'-phosphate oligonucleotides by the appearance of new bands. Ligation was effective with chimeras having 6 PNA monomers and from 2 to 4 2'-deoxynucleotide monomers. Control ligation between two oligonucleotide probes (lane 2) shows a ligation product band. Control ligation with only one probe (lanes 1,5,7,9) does not show a new band. Experiments without T4 ligase (bottom gel image) show bands for the templates and probes.

TABLE 2

FIGS. 4A–4B

| Lane | Template | PNA-DNA chimera or oligonucleotide | 5'-phosphate oligonucleotide |
| --- | --- | --- | --- |
| 1 | DNA1 | | DNA2 |
| 2 | DNA1 | DNA3 | DNA2 |
| 3 | DNA1 | $PNA_6$-$DNA_3$ | DNA2 |
| 4 | DNA1 | $PNA_6$-$DNA_3$ | DNA2 |
| 5 | DNA1 | | DNA4 |
| 6 | DNA1 | $PNA_6$-$DNA_2$ | DNA4 |
| 7 | DNA1 | | DNA5 |
| 8 | DNA1 | $PNA_6$-$DNA_4$ | DNA5 |
| 9 | DNA6 | | DNA5 |
| 10 | DNA6 | $PNA_{11}$-$DNA_4$ | DNA5 |
| M | DNA oligo ladder | | |

DNA1 Biotin-cgctcaacacatagcatggtctagaactaag-cctggaa (SEQ. ID NO. 9)

DNA6 cgctcaacacatagcatggtaaagccgggacct-

| | |
|---|---|
| aactgtt | (SEQ. ID NO. 15) |
| DNA3 tagttctag | (SEQ. ID NO. 2) |
| PNA$_6$-DNA$_2$ TAGTTC-ta | (SEQ; ID NO. 5) |
| PNA$_6$-DNA$_3$ TAGTTC-tag | (SEQ. ID NO. 6) |
| PNA$_6$-DNA$_4$ TAGTTC-taga | (SEQ. ID NO. 7) |
| PNA$_{11}$-DNA$_4$ TAGGTCCCGGC-ttta | (SEQ. ID NO. 10) |
| DNA2 5'-phos accatgctatgtgttgagcg | (SEQ. ID NO. 11) |
| DNA4 5'-phos-gaccatgctatgtgttgagcg-biotin | (SEQ.ID NO. 12) |
| DNA5 5'-phos-ccatgctatgtgttgagcg-biotin | (SEQ. ID NO. 8) |

(UPPER CASE—PNA, lower case—DNA)

FIG. 4B shows the quantitative estimate of the ligase reactions in FIG. 4A by densitometry with the SpotDenso program. The bands enclosed by the boxes are the 5'-phosphate probes remaining after ligation. The negative control experiments in lane 1,5,7, and 9 established the levels of 5'-phosphate probe remaining when no ligation occurred. The positive control experiment in lane 2 gave the ligation efficiency between two all-DNA probes. From these quantified values, the ligation efficiencies with PNA-DNA chimeric probes can be calculated from the areas (IDV—Integrated Density Value) in the chart (right).

FIG. 5 shows ligation experiments using T4 DNA ligase with PNA-DNA chimeric probes to which 1 to 4 DNA bases are attached at 3' terminus of the PNA oligomer and a second probe, a 5'-phosphate oligonucleotide of variable lengths (lanes 4–7). The lengths of the chimera and the oligonucleotide probes are chosen to form ligation products of equivalent length (Table 3). In addition, control ligations were conducted where instead of the chimera, no probe (lane 2), an all PNA probe (lane 3), an all-DNA probe, 6 nt (lane 8) and an all-DNA probe, 9 nt (lane 9) were used. The ligation mixture contained a 38 nt DNA template and the two probes at a final concentration of 1 µM each, 1×T4 DNA ligase buffer [50 mM Tris-HCl, pH 7.5, 10 mM McgCl$_2$, 10 mM dithiothreitol, 1 mM ATP, 25 µg/ml bovine serum albumin], and 100 units of T4 DNA ligase in a volume of 50 µl. The ligation reaction mixture was incubated at 22.5 to 25° C. for 3 to 4 h. After incubation, the reaction mixture was heated at 80° C. for 20 min and then stored at 4° C. Five µl of the reaction mixture was loaded onto a 15% polyacrylamide gel and electrophoresed at 120–140 V under denaturing conditions (7M urea, 70° C.) for 20–60 min., then stained with SYBR-Green. FIG. 5A shows a scanned image of the stained gel. FIG. 5B is a schematic of ligation of PNA, PNA-DNA chimera, and DNA to 5'-phosphate oligonucleotides hybridized to a DNA template 38 nt (SEQ. ID NO. 9).

It is evident from new bands below the template bands that PNA-DNA chimeras are ligated where the chimera has 2, 3, or 4 DNA monomers (2'-deoxynucleotides), lanes 5–7 respectively. No ligation is evident for an all-PNA probe or a chimera containing only 1 DNA monomer, lanes 3 and 4 respectively. Lane 1 is a negative control. Lanes 8 and 9 are positive controls, where 6 nt and 9 nt oligonucleotides are ligated to 5'-phosphate oligonucleotides. The electrophoretic retardation of PNA in the ligation products of chimera, lanes 5–7, is evident compared to all-DNA ligation products, lanes 8 and 9.

TABLE 3

FIGS. 5A–5B

| | | Probes | |
|---|---|---|---|
| Lane | DNA Template | 5'-phosphate DNA | PNA-DNA chimera |
| 2 | 38 nt | 23 nt | None |
| 3 | 38 nt | 23 nt | PNA$_6$ |
| 4 | 38 nt | 22 nt | PNA$_6$-DNA$_1$ |
| 5 | 38 nt | 21 nt | PNA$_6$-DNA$_2$ |
| 6 | 38 nt | 20 nt | PNA$_6$-DNA$_3$ |
| 7 | 38 nt | 19 nt | PNA$_6$-DNA$_4$ |
| 8 | 38 nt | 23 nt | DNA$_6$ |
| 9 | 38 nt | 20 nt | DNA$_9$ |
| 1 | M = DNA oligonucleotide ladder | | |

| | |
|---|---|
| DNA$_6$ tagttc | (SEQ. ID NO. 1) |
| DNA$_9$ tagttctag | (SEQ. ID NO. 2) |
| PNA$_6$ TAGTTC | (SEQ. ID NO. 3) |
| PNA$_6$-DNA$_1$ TAGTTC-t | (SEQ. ID NO. 4) |
| PNA$_6$-DNA$_2$ TAGTTC-ta | (SEQ. ID NO. 5) |
| PNA$_6$-DNA$_3$ TAGTTC-tag | (SEQ. ID NO. 6) |
| PNA$_6$-DNA$_4$ TAGTTC-taga | (SEQ. ID NO. 7) |

5'-phosphate oligos:

| | |
|---|---|
| 19 nt 5'-phos-ccatgctatgtgttgagcg-biotin | (SEQ. ID NO. 8) |
| 20 nt 5'-phos-accatgctatgtgttgagcg-biotin | (SEQ.ID NO. 11) |
| 21 nt 5'-phos-gaccatgctatgtgttgagcg-biotin | (SEQ.ID NO.12) |
| 22 nt 5'-Phos-agaccatgctatgtgttgagcg-biotin | (SEQ. ID NO. 13) |
| 23 nt 5'-Phos-tagaccatgctatgtgttgagcg-biotin | (SEQ. ID NO.14) |
| DNA template 38 nt: cgctcaacacatagcatggtc-agaactaagcctqgaa | (SEQ. ID NO. 16) |

(UPPER CASE—PNA, lower case—DNA)

FIG. 6 shows the specificity of ligation with PNA-DNA chimeric probes. PNA-DNA chimeras and 5'-phosphate oligonucleotides were ligated on templates, as perfect matches and with mismatches. Ligation mixtures contained a template and two probes at a final concentration of 1 µM each, 1×T4 DNA ligase buffer [50 mM Tris-HCl, pH 7.5, 10 mM MgCl$_2$, 10 mM dithiothreitol, 1 mM ATP, 25 µg/ml bovine serum albumin], and 1,000 units of T4 DNA ligase in a volume of 50 µl. Ligation reactions were incubated at 22.5 to 25° C. for 3 to 4 h. After incubation, the reaction mixture was heated at 80° C. for 20 min and then stored at 4° C. Five µl of the reaction mixture was used for PAGE analysis, electrophoresing at 120–140 V for 20–60 min.

TABLE 4

| | | | FIG. 6 | |
|---|---|---|---|---|
| | | Phosphorylated DNA | | PNA-DNA chimera or DNA |
| Lane | DNA Template | Matched | Mismatched | oligonucleotide |
| 1 | DNA1C | DNA2 | | DNA$_9$ |
| 2 | DNA1C | DNA2 | DNA2A | DNA$_9$ |

TABLE 4-continued

| | | | FIG. 6 PNA-DNA chimera |
|---|---|---|---|
| | | Phosphorylated DNA | or DNA |
| Lane | DNA Template | Matched Mismatched | oligonucleotide |
| 3 | DNA1C | DNA2 | $PNA_6$-$DNA_3$ |
| 4 | DNA1C | DNA2  DNA2A | $PNA_6$-$DNA_3$ |
| 5 | DNA1C | DNA3 | $PNA_6$-$DNA_4$ (mismatched) |
| 6 | DNA2C | DNA2A | $DNA_9$ (mismatched) |
| 7 | DNA2C | DNA2A | $PNA_6$-$DNA_3$ (mismatched) |
| 8 | DNA2C | DNA4 | $PNA_6$-$DNA_2$ (mismatched) |
| M | DNA oligo-nucleotide ladder | | |

DNA Template

DNA1C Biotin-cgctcaacacatagcatggcctagaa-ctaagcctggaa  (SEQ. ID NO. 27)

DNA2C Biotin-cgctcaacacatagcatggtccagaa-ctaagcctggaa  (SEQ. ID NO. 16)

Phosphorylated DNA

DNA2 5'-Phos-gccatgctatgtgtt-Biotin  (SEQ. ID NO. 17)

DNA2A 5'-Phos-accatgctatgtgtt-Biotin  (SEQ. ID NO. 18)

DNA3 5'-Phos-ccatgctatgtgttgagcg-Biotin  (SEQ. ID NO. 8)

DNA3 5'-Phos-accatgctatgtgttgagcg-Biotin  (SEQ. ID NO. 11)

DNA $DNA_9$ tagttctag  (SEQ. ID NO. 2)

PNA-DNA Chimera $PNA_6$-$DNA_2$ TAGTTC-ta  (SEQ. ID NO. 5)

$PNA_6$-$DNA_3$ TAGTTC-tag  (SEQ. ID NO. 6)

$PNA_6$-$DNA_4$ TAGTTC-taga  (SEQ. ID NO. 7)

(UPPER CASE—PNA, lower case—DNA)

The experiments in FIG. 6 show that PNA-DNA chimeric probes require a high level of sequence complementarity for ligation to occur. When a mismatch occurs either in the chimeric probe or the second probe, ligation is not detectable, within the limits of the system shown. By comparison, all-DNA probes are less specific. When a mismatch occurs in either all-DNA probe, some ligation is still evident. Lane 1 is a positive control ligation where two oligonucleotides are perfectly matched (W) to the template and ligate to form a ligation product migrating at the expected rate of 24 nt. The experiment of lane 2 additionally has a mismatched (W+M) probe which ligates, evidenced by a new band between the perfect match product and the template (38 nt). The mismatched probe, DNA2A, has a mismatch at the ligation site, the A base at the 5' terminus of the 5'-phosphate probe. The experiment of lane 3 ligates perfectly matched $PNA_6$-$DNA_3$ chimera and DNA2 second probe, giving a new band, migrating faster than template. The experiment of lane 4 additionally has the mismatched DNA2A probe. Unlike the all-DNA experiment of lane 2, mismatched DNA2A does not ligate with the chimera, demonstrating greater specificity conferred by the PNA moiety. The experiments of lanes 5 and 7 likewise have mismatches at the 3' terminus of the chimera. The 3' terminus of the chimera in the experiment of lane 8 has a deletion and a mismatch. These experiments, lanes 5,7,8 show no ligation product. The experiment of lane 6 has a mismatch in the $DNA_9$ probe at the penultimate base near the 3' terminus. In this experiment, a ligation product is evident, reflecting the lower specificity of ligation of all-DNA probes.

In summary, the ligation experiments shown in FIG. 6 illustrate that PNA-DNA chimeric probes when ligated to oligonucleotide probes are better able to discriminate base-pair mismatches (specificity) than ligations between two all-DNA, oligonucleotide probes, whether the mismatch occurs in the chimera probe or the oligonucleotide probe.

Example 3

MALDI-TOF Analysis of Ligation Reaction

Mass spectra were acquired on a MALDI-TOF MS (Voyager DE, PerSeptive Biosystems, division of PE Corporation) workstation. Desalted samples are mixed 1:1 with matrix solution consisting of 50 mg/ml 3-hydroxy picolinic acid, 50 mM ammonium citrate, and 30% acetonitrile, and are spotted onto a sample plate. Time-of-flight data from 20 to 50 individual laser pulses are recorded and averaged on a transient digitizer, after which the averaged spectra are automatically converted to mass by data processing software. FIG. 7 of ligation reactions. A 3' biotinylated 20 nt oligonucleotide (mass 6303) and a PNA-DNA chimera (mass 2539) were hybridized to 5' biotinylated DNA template 38 nt (mass 12358). FIG. 7A shows MALDI-TOF Mass Spectroscopy analysis of the mixture without ligase. The analysis shows only ion peaks of the starting materials. When the ligation mixture contains ligase (FIG. 7B), a ligation product is evident with the expected mass of 8823.8.

template: Biotin-cgctcaacacatagcatggtctagaact-aagcctggaa  (SEQ. ID NO. 9)

5'-phos-accatgctatgtgttgagcg-biotin (mass 6303)  (SEQ. ID NO. 11)

Ac-TAGTTC-tag (mass 2539)  (SEQ. ED NO. 6)

ligation product: Ac-TAGTTC-tagaccatgctatgtgttgagcg-biotin (mass 8824)  (SEQ. ID NO. 19)

Ac=acetylated amino terminus (UPPER CASE—PNA, lower case—DNA)

Example 4 Multiplex Oligonucleotide Ligation Assay for CFTR Loci

OLA reactions for CFTR loci were multiplexed in one tube. Two differentially labelled (i.e. FAM- or TET- at 5' site) PNA-DNA chimeras and one 5' phosphorylated DNA oligonucleotide were used for the analysis of each mutation. The sequences of the probes and templates are given in FIG. 8. All multiplex OLA reactions are carried in a 20 µl reaction volume containing 20 mM Tris-HCl, pH 7.6, 25 mM potassium acetate, 10 mM magnesium acetate, 10 mM DTT, 1 mM NAD, 0.1% Triton X-100, 1 to 50 nM each probe, 5 to 10 µl of pooled PCR product, and 2 to 10 units of thermostable ligase such as *Thermus aquaticus* ligase. Linear amplification of product is achieved by 20 to 30 cycles at 94° C. for 30 sec and 30 to 50° C. for 1 to 3 min, followed by heating at 95° C. for 10 to 20 min in a Model 9700 Thermocycler (PE Biosystems division of PE Corporation).

An aliquot of 2 µl of each multiplex OLA product was mixed with 2.5 µl of deionized formamide, 0.5 µl of dextran blue loading buffer, and 0.5 µl of GENESCAN-500 TAMRA size marker. The mixture was denatured at 95° C. for 3 min and then rapidly chilled on ice prior to loading the gel. OLA products were electrophoresed for 3.5 h at 2,500 V on a Model 373A fluroescence-scanning DNA sequencer (PE Biosystems, division of PE Corporation) using an 8% acrylamide, 19:1 acrylamide:bisacrylamide, denaturing gel containing 8.3 M urea, 89 mM Tris, 89 mM boric acid, and 2 mM EDTA. The resulting gel data are analyzed for peak color and fragment size using the GENESCAN Fragment Analysis Software and the Genotyper Software (PE Biosystems Division of PE Corporation).

Figure 9D:
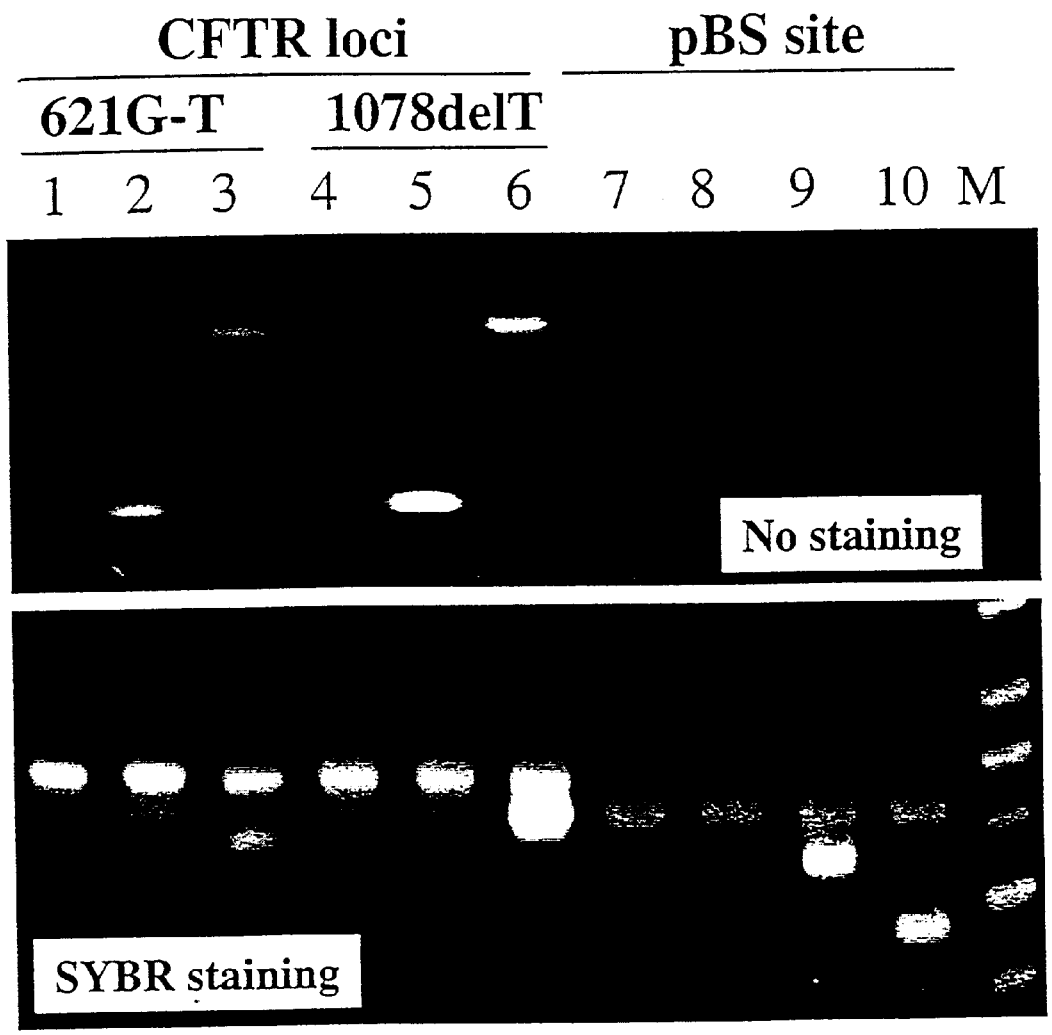
Figure 9D:
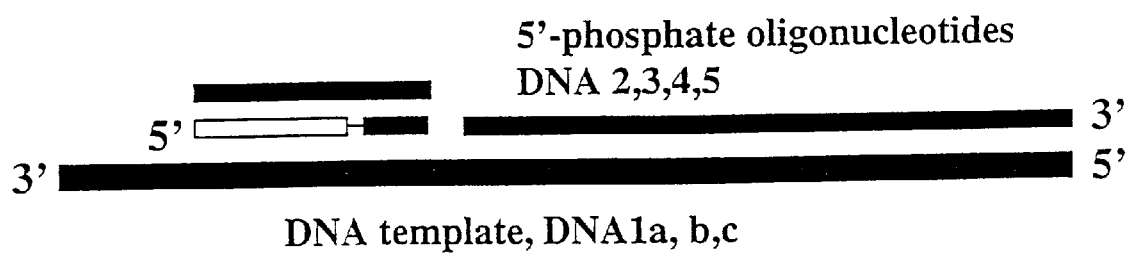
Figure 9D:
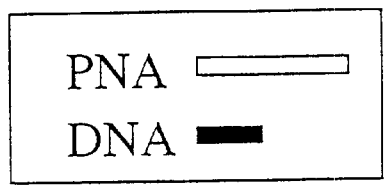

FIG. 9 shows the oligonucleotide ligation assay with PNA-DNA chimera probes to discriminate mutations in human CFTR loci. Ligation mixtures contained a template and two probes at a final concentration of 1 µM each, 1×T4 DNA ligase buffer [50 mM Tris-HCl, pH 7.5, 10 mM MgCl$_2$, 10 mM dithiothreitol, 1 mM ATP, 25 µg/ml bovine serum albumin], and 1,000 units of T4 DNA ligase (New England Biolabs) plus 10 units of T4 polynucleotide kinase in a volume of 50 µl. The mixtures were incubated at 22.5 to 25° C. for 3 to 4 h. After incubation the reaction mixture was heated at 80° C. for 20 min and then stored at 4° C. Five µl of the reaction mixture was used for PAGE analysis, electrophoresing at 120–140 V for 20–60 min (9A) human pCFTR621G-T: Exon 4; (9B) human pCFTR1078delT: Exon 7; (9C) human pCFTRGG551D: Exon 11. (UPPER CASE—PNA, lower case—DNA)

FIG. 9D shows scanned images of OLA experiments with PNA-DNA chimeric probes and an all-DNA control probe (lane 10). Ligation of a 3'-TAMRA-labelled, 5'-phosphate oligonucleotide with PNA$_{10}$-DNA$_3$ chimera at the CFTR locus 621G-T with T4 ligase gave a fluorescent labelled product, visible without staining under UV light (9D, top gel) and by staining with SYBR-Green (9D, bottom gel). Ligation products with PNA-DNA chimeric probes are also evident from experiments in lanes 3 and 9.

TABLE 5

| | FIG. 9D | | |
|---|---|---|---|
| Lane | DNA template | PNA-DNA chimera or oligonucleotide | 5'-phosphate oligonucleotide |
| 1 | 1a | | |
| 2 | 1a | | 2 (FAM) |
| 3 | 1a | PNA$_{10}$-DNA$_3$ | 2 |
| 4 | 1b | | |
| 5 | 1b | | 3 (TAMRA) |

TABLE 5-continued

| | FIG. 9D | | |
|---|---|---|---|
| Lane | DNA template | PNA-DNA chimera or oligonucleotide | 5'-phosphate oligonucleotide |
| 6 | 1b | PNA$_{10}$-DNA$_3$ | 3 (TAMRA) |
| 7 | 1c | | |
| 8 | 1c | | 4 |
| 9 | 1c | PNA$_6$-DNA$_4$ | 4 |
| 10 | 1c | DNA$_9$ | 4 |
| M | DNA oligo ladder | | |

DNA Template

| | | |
|---|---|---|
| DNA1a | gtttgatttataagaaggtaatacttccttgcacag | (SEQ. ID NO. 20) |
| DNA1b | cacagataaaaacaccacaaagaaccctqaqaa-gaagaag | (SEQ. ID NO. 21) |
| DNA1c | Biotin-cgctcaacacatagcatggtctagaact-aagcctggaa | (SEQ. ID NO. 9) |

PNA-DNA Chimera

| | | |
|---|---|---|
| PNA$_{10}$-DNA$_3$ (lane 3) | Ac-CAAGGAAGTA-tta | (SEQ. ID NO. 22) |
| PNA$_{10}$-DNA$_3$ (lane 6) | Ac-CTTCTCAGGG-ttc | (SEQ. ID NO. 23) |
| PNA$_6$-DNA$_4$ | TAGTTC-taga | (SEQ. ID NO. 7) |

DNA

| | | |
|---|---|---|
| DNA$_9$ | tagttctag | (SEQ. ID NO. 2) |

5'-phosphate oligonucleotides

| | | |
|---|---|---|
| 2(FAM) | 5'-Phos-ccttcttata-FAM-3' | (SEQ. ID NO. 24) |
| 2 | 5'-Phos-ccttcttata-3' | (SEQ. ID NO. 24) |
| 3(TAMRA) | 5'-Phos-tttgtggtgtttt-TAMRA-3' | (SEQ. ID NO. 25) |
| 4 | 5'-Phos-ccatgctatgtgtt-Biotin-3' | (SEQ. ID NO. 26) |

All publications and patent applications are herein incorporated by reference to the same extent as if each individual publication or patent application was specifically and individually indicated to be incorporated by reference.

Although certain embodiments have been described in detail above, those having ordinary skill in the art will clearly understand that many modifications are possible in the preferred embodiments without departing from the teachings thereof. All such modifications are intended to be encompassed within the following claims.

We claim:

1. An array of PNA-DNA chimeric probes comprising a plurality of PNA-DNA chimeric probes immobilized on a solid substrate where a chimeric probe of known sequence occupies a defined area and said chimeric probes have the formula:

$$P_x\text{-}L\text{-}N_y$$

wherein:

$P_x$ is a PNA moiety and each P is independently a PNA monomer;

x is an integer from 3 to 15;

$N_y$ is a DNA moiety and each N is independently a nucleotide;

y is an integer of 2 or more; and

L represents a covalent linkage between P and N;

with the proviso that the terminal nucleotide N has a 3'-hydroxyl or phosphate group or a 5'-hydroxyl or phosphate group, whereby the DNA moiety is capable of ligation;

and wherein the chimeric probe is covalently attached by a linker at a terminus of the PNA moiety to the solid substrate.

2. The array of chimeric probes of claim 1 wherein the probes are immobilized on beads or particles contained in wells or vessels.

3. The array of chimeric probes of claim 1 wherein the solid substrate is selected from polystyrene, controlled-pore-glass, glass, silica gel, silica, polyacrylamide, magnetic beads, polyacrylate, hydroxyethylmethacrylate, polyamide, polyethylene, polyethyleneoxy, and copolymers and grafts of any of the above solid substrates.

4. The array of chimeric probes of claim 1 wherein the solid substrate is selected from small particles, beads, membranes, a frit, a slide, a plate, a micromachined chip, an alkanethiol-gold layer, a non-porous surface, and polynucleotide-immobilizing media.

5. The array of chimeric probes of claim 1 wherein L is selected from a covalent bond, phosphate, phosphoramidate, alkyldiyl consisting of 1–20 carbon atoms, aryldiyl consisting of 6–20 carbon atoms, O-linker, and —$(CH_2CH_2O)_m$— where m is 1 to 6.

6. The array of chimeric probes of claim 1 further comprising a second probe which is a PNA-DNA chimera or an oligonucleotide, and a template nucleic acid with a sequence complementary to the PNA-DNA chimeric probe or containing one or more mismatches relative to the chimeric probe,
wherein a terminus of the second probe hybridizes adjacent to a terminus of the PNA-DNA chimeric probe on the template, and
wherein at least a portion of the PNA moiety of the PNA-DNA chimeric probe hybridizes to the template.

7. A method of array ligation comprising:
a) providing an array of a plurality of PNA-DNA chimeric probes immobilized on a solid substrate where a PNA-DNA chimeric probe of known sequence occupies a defined area on the solid substrate and said PNA-DNA chimeric probes have the formula:

$P_x$-L-$N_y$ wherein:
$P_x$ is a PNA moiety and each P is independently a PNA monomer;
x is an integer from 3 to 15;
$N_y$ is a DNA moiety and each N is independently a nucleotide;
y is an integer of 2 or more; and
L represents a covalent linkage between P and N;
with the proviso that the terminal nucleotide N has a 3'-hydroxyl group or a 5'-hydroxyl group;
b) hybridizing a second probe and a template nucleic acid to one or more of the PNA-DNA chimeric probes of the array wherein the PNA-DNA chimeric probe and the second probe are each hybridized to the template nucleic acid and adjacent to each other, and at least a portion of the PNA moiety of the PNA-DNA chimeric probe is hybridized to the template, and wherein the second probe is a PNA-DNA chimera or an oligonucleotide; and
c) ligating the PNA-DNA chimeric probe to the second probe which are hybridized to the template nucleic acid.

8. The method of array ligation of claim 7 wherein ligation is effected by a ligase enzyme.

9. The method of array ligation of claim 8 wherein the ligase is selected from T4 DNA ligase, *E. coli* DNA ligase, RNA ligase, and a thermostable ligase.

10. The method of array ligation of claim 7 further comprising removing unhybridized probes and template nucleic acids by washing under conditions that maintain hybridization.

11. The method of array ligation of claim 7 wherein the second probe is covalently attached to a non-radioisotopic label.

12. The method of array ligation of claim 11 wherein the non-radioisotopic label is a fluorescent dye, whereby a fluorescent labelled ligation product is covalently immobilized on the surface.

13. The method of array ligation of claim 12 further comprising detecting the fluorescent labelled ligation product.

14. A method of array ligation comprising:
a) providing an array of a plurality of immobilized probes assembled on a solid substrate wherein an immobilized probe of known sequence occupies a defined area on the solid substrate, and wherein the immobilized probe is a PNA-DNA chimera or an oligonucleotide;
b) hybridizing one or more PNA-DNA chimeric probes and one or more template nucleic acids to one or more of the immobilized probes of the array wherein a PNA-DNA chimeric probe and an immobilized probe are each hybridized to the template nucleic acid and adjacent to each other, and at least a portion of the PNA moiety of the PNA-DNA chimeric probe is hybridized to the template, wherein said PNA-DNA chimeric probe has the formula:

$P_x$-L-$N_y$ wherein:
$P_x$ is a PNA moiety and each P is independently a PNA monomer;
x is an integer from 3 to 15;
$N_y$ is a DNA moiety and each N is independently a nucleotide; and
y is an integer of 2 or more;
L represents a covalent linkage between P and N;
with the proviso that the terminal nucleotide N has a 3'-hydroxyl group or a 5'-hydroxyl group; and
c) ligating the PNA-DNA chimeric probe to the immobilized probe which are hybridized to the template nucleic acid.

15. A method of array ligation comprising:
a) providing an array of a plurality of template nucleic acids immobilized on a solid substrate wherein a template nucleic acid of unique sequence occupies a defined area on the solid substrate;
b) hybridizing one or more PNA-DNA chimeric probes and one or more second probes to one or more of the immobilized template nucleic acids of the array wherein a PNA-DNA chimeric probe and a second probe are each hybridized to the template nucleic acid and adjacent to each other, and at least a portion of the PNA moiety of the PNA-DNA chimeric probe is hybridized to the template, wherein the second probe is a PNA-DNA chimera or an oligonucleotide and said PNA-DNA chimeric probe has the formula:

$P_x$-L-$N_y$ wherein:
$P_x$ is a PNA moiety and each P is independently a PNA monomer;
x is an integer from 3 to 15;
N is a DNA moiety and each N is independently a nucleotide; and
y is an integer of 2 or more;
L represents a covalent linkage between P and N;

with the proviso that the terminal nucleotide N has a 3'-hydroxyl group or a 5'-hydroxyl group; and c) ligating the PNA-DNA chimeric probe to the second probe which are hybridized to the immobilized template nucleic acid.

16. The array of PNA-DNA chimeric probes of claim 1 wherein one or more of the PNA-DNA chimeric probes comprises a label selected from a fluorescent dye, a fluorescence quencher, a hybridization-stabilizer, an energy-transfer dye set, an electrophoretic mobility modifier, a chemiluminescent dye, an amino acid, a protein, a peptide, and an affinity ligand.

17. The array of PNA-DNA chimeric probes of claim 6 wherein the second probe or the template nucleic acid comprises a label selected from a fluorescent dye, a fluorescence quencher, a hybridization-stabilizer, an energy-transfer dye set, an electrophoretic mobility modifier, a chemiluminescent dye, an amino acid, a protein, a peptide, and an affinity ligand.

* * * * *

SEQUENCE LISTING

<160> NUMBER OF SEQ ID NOS: 27

<210> SEQ ID NO 1
<211> LENGTH: 6
<212> TYPE: DNA
<213> ORGANISM: Unknown Organism
<220> FEATURE:
<223> OTHER INFORMATION: Description of Unknown Organism: Bacterial

<400> SEQUENCE: 1

```
tagttc                                                              6

<210> SEQ ID NO 2
<211> LENGTH: 9
<212> TYPE: DNA
<213> ORGANISM: Unknown Organism
<220> FEATURE:
<223> OTHER INFORMATION: Description of Unknown Organism: Bacterial

<400> SEQUENCE: 2 tagttctag                                                           9

<210> SEQ ID NO 3
<211> LENGTH: 6
<212> TYPE: DNA
<213> ORGANISM: Unknown Organism
<220> FEATURE:
<223> OTHER INFORMATION: Description of Unknown Organism: Bacterial

<400> SEQUENCE: 3 tagttc                                                              6

<210> SEQ ID NO 4
<211> LENGTH: 7
<212> TYPE: DNA
<213> ORGANISM: Unknown Organism
<220> FEATURE:
<223> OTHER INFORMATION: Description of Unknown Organism: Bacterial

<400> SEQUENCE: 4 tagttct                                                             7

<210> SEQ ID NO 5
<211> LENGTH: 8
<212> TYPE: DNA
<213> ORGANISM: Unknown Organism
<220> FEATURE:
<223> OTHER INFORMATION: Description of Unknown Organism: Bacterial

<400> SEQUENCE: 5 tagttcta                                                            8

<210> SEQ ID NO 6
<211> LENGTH: 9
<212> TYPE: DNA
<213> ORGANISM: Unknown Organism
<220> FEATURE:
<223> OTHER INFORMATION: Description of Unknown Organism: Bacterial

<400> SEQUENCE: 6 tagttctag                                                           9

<210> SEQ ID NO 7
<211> LENGTH: 10
<212> TYPE: DNA
<213> ORGANISM: Unknown Organism
<220> FEATURE:
<223> OTHER INFORMATION: Description of Unknown Organism: Bacterial

<400> SEQUENCE: 7
tagttctaga                                                         10

<210> SEQ ID NO 8
<211> LENGTH: 19
<212> TYPE: DNA
<213> ORGANISM: Unknown Organism
```

```
<220> FEATURE:
<223> OTHER INFORMATION: Description of Unknown Organism: Bacterial

<400> SEQUENCE: 8
ccatgctatg tgttgagcg                                                19

<210> SEQ ID NO 9
<211> LENGTH: 38
<212> TYPE: DNA
<213> ORGANISM: Unknown Organism
<220> FEATURE:
<223> OTHER INFORMATION: Description of Unknown Organism: Bacterial

<400> SEQUENCE: 9
cgctcaacac atagcatggt ctagaactaa gcctggaa                            38

<210> SEQ ID NO 10
<211> LENGTH: 15
<212> TYPE: DNA
<213> ORGANISM: Unknown Organism
<220> FEATURE:
<223> OTHER INFORMATION: Description of Unknown Organism: Bacterial

<400> SEQUENCE: 10
taggtcccgg cttta                                                    15

<210> SEQ ID NO 11
<211> LENGTH: 20
<212> TYPE: DNA
<213> ORGANISM: Unknown Organism
<220> FEATURE:
<223> OTHER INFORMATION: Description of Unknown Organism: Bacterial

<400> SEQUENCE: 11
accatgctat gtgttgagcg                                               20

<210> SEQ ID NO 12
<211> LENGTH: 21
<212> TYPE: DNA
<213> ORGANISM: Unknown Organism
<220> FEATURE:
<223> OTHER INFORMATION: Description of Unknown Organism: Bacterial

<400> SEQUENCE: 12
gaccatgcta tgtgttgagc g                                             21

<210> SEQ ID NO 13
<211> LENGTH: 22
<212> TYPE: DNA
<213> ORGANISM: Unknown Organism
<220> FEATURE:
<223> OTHER INFORMATION: Description of Unknown Organism: Bacterial

<400> SEQUENCE: 13
agaccatgct atgtgttgag cg                                            22

<210> SEQ ID NO 14
<211> LENGTH: 23
<212> TYPE: DNA
<213> ORGANISM: Unknown Organism
<220> FEATURE:
<223> OTHER INFORMATION: Description of Unknown Organism: Bacterial

<400> SEQUENCE: 14
tagaccatgc tatgtgttga gcg                                           23
```

<210> SEQ ID NO 15
<211> LENGTH: 40
<212> TYPE: DNA
<213> ORGANISM: Unknown Organism
<220> FEATURE:
<223> OTHER INFORMATION: Description of Unknown Organism: Bacterial

<400> SEQUENCE: 15
cgctcaacac atagcatggt aaagccggga cctaactgtt                          40

<210> SEQ ID NO 16
<211> LENGTH: 38
<212> TYPE: DNA
<213> ORGANISM: Unknown Organism
<220> FEATURE:
<223> OTHER INFORMATION: Description of Unknown Organism: Bacterial

<400> SEQUENCE: 16
cgctcaacac atagcatggt ccagaactaa gcctggaa                            38

<210> SEQ ID NO 17
<211> LENGTH: 15
<212> TYPE: DNA
<213> ORGANISM: Unknown Organism
<220> FEATURE:
<223> OTHER INFORMATION: Description of Unknown Organism: Bacterial

<400> SEQUENCE: 17
gccatgctat gtgtt                                                    15

<210> SEQ ID NO 18
<211> LENGTH: 15
<212> TYPE: DNA
<213> ORGANISM: Unknown Organism
<220> FEATURE:
<223> OTHER INFORMATION: Description of Unknown Organism: Bacterial

<400> SEQUENCE: 18
accatgctat gtgtt                                                    15

<210> SEQ ID NO 19
<211> LENGTH: 31
<212> TYPE: DNA
<213> ORGANISM: Unknown Organism
<220> FEATURE:
<223> OTHER INFORMATION: Description of Unknown Organism: Bacterial

<400> SEQUENCE: 19
actagttcta gaccatgcta tgtgttgagc g                                  31

<210> SEQ ID NO 20
<211> LENGTH: 36
<212> TYPE: DNA
<213> ORGANISM: Human CFTR

<400> SEQUENCE: 20
gtttgattta taagaaggta atacttcctt gcacag                             36

<210> SEQ ID NO 21
<211> LENGTH: 40
<212> TYPE: DNA
<213> ORGANISM: Human CFTR

<400> SEQUENCE: 21
cacagataaa aacaccacaa agaaccctga gaagaagaag                         40

```
<210> SEQ ID NO 22
<211> LENGTH: 15
<212> TYPE: DNA
<213> ORGANISM: Human CFTR

<400> SEQUENCE: 22
accaaggaag tatta                                                15

<210> SEQ ID NO 23
<211> LENGTH: 15
<212> TYPE: DNA
<213> ORGANISM: Human CFTR

<400> SEQUENCE: 23
accttctcag ggttc                                                15

<210> SEQ ID NO 24
<211> LENGTH: 10
<212> TYPE: DNA
<213> ORGANISM: Human CFTR

<400> SEQUENCE: 24
ccttcttata                                                      10

<210> SEQ ID NO 25
<211> LENGTH: 13
<212> TYPE: DNA
<213> ORGANISM: Human CFTR

<400> SEQUENCE: 25
tttgtggtgt ttt                                                  13

<210> SEQ ID NO 26
<211> LENGTH: 14
<212> TYPE: DNA
<213> ORGANISM: Human CFTR

<400> SEQUENCE: 26
ccatgctatg tgtt                                                 14

<210> SEQ ID NO 27
<211> LENGTH: 38
<212> TYPE: DNA
<213> ORGANISM: Unknown Organism
<220> FEATURE:
<223> OTHER INFORMATION: Description of Unknown Organism: Bacterial

<400> SEQUENCE: 27
cgctcaacac atagcatggc ctagaactaa gcctggaa                       38
```